(12) United States Patent
Desai et al.

(10) Patent No.: US 8,927,019 B2
(45) Date of Patent: Jan. 6, 2015

(54) METHODS AND COMPOSITIONS FOR TREATING RECURRENT CANCER

(75) Inventors: Neil P. Desai, Los Angeles, CA (US); Patrick Soon-Shiong, Los Angeles, CA (US)

(73) Assignee: Abraxis Bioscience, LLC, Los Angeles, CA (US)

( * ) Notice: Subject to any disclaimer, the term of this patent is extended or adjusted under 35 U.S.C. 154(b) by 708 days.

(21) Appl. No.: 12/600,991

(22) PCT Filed: Jun. 2, 2008

(86) PCT No.: PCT/US2008/007024
§ 371 (c)(1),
(2), (4) Date: May 10, 2010

(87) PCT Pub. No.: WO2008/150532
PCT Pub. Date: Dec. 11, 2008

(65) Prior Publication Data
US 2010/0215751 A1    Aug. 26, 2010

Related U.S. Application Data

(60) Provisional application No. 60/932,750, filed on Jun. 1, 2007.

(51) Int. Cl.
*A61K 31/337* (2006.01)
*A61P 35/00* (2006.01)
*A61K 9/51* (2006.01)
*A61K 31/555* (2006.01)
*A61K 38/38* (2006.01)
*A61K 47/48* (2006.01)

(52) U.S. Cl.
CPC ............ *A61K 9/5169* (2013.01); *A61K 31/337* (2013.01); *A61K 31/555* (2013.01); *A61K 38/38* (2013.01); *A61K 47/48284* (2013.01); *A61K 47/48884* (2013.01); *Y10S 977/773* (2013.01); *Y10S 977/906* (2013.01)
USPC ............ 424/489; 514/449; 977/773; 977/906

(58) Field of Classification Search
CPC ............... A61K 37/337; A61K 38/38; A61K 47/48284; A61K 9/5169
USPC .................... 424/489; 514/449; 977/773, 906
See application file for complete search history.

(56) References Cited

U.S. PATENT DOCUMENTS

| | | | |
|---|---|---|---|
| 5,206,018 | A | 4/1993 | Sehgal et al. |
| 5,362,478 | A | 11/1994 | Desai et al. |

(Continued)

FOREIGN PATENT DOCUMENTS

| | | |
|---|---|---|
| EP | 1 683 517 A1 | 7/2006 |
| JP | 2004-525950 A | 8/2004 |

(Continued)

OTHER PUBLICATIONS

Green et al.,"Abraxane, a novel cremophor-free, albumin-bound particle form of paclitaxel for the treatment of advanced non-small-cell lung cancer," Annals of Oncology Advance Access, pp. 1-6, Jun. 1, 2006.*

(Continued)

*Primary Examiner* — Rachael E Bredefeld
(74) *Attorney, Agent, or Firm* — Morrison & Foerster LLP

(57) ABSTRACT

The present invention provides methods of treating recurrent cancer (such as recurrent ovarian, peritoneal, or fallopian tube cancer) in an individual, comprising administering to the individual an effective amount of a composition (such as Nab-paclitaxel or Abraxane®) comprising nanoparticles comprising a taxane and a carrier protein.

29 Claims, 3 Drawing Sheets

(56) References Cited

U.S. PATENT DOCUMENTS

| | | |
|---|---|---|
| 5,439,686 A | 8/1995 | Desai et al. |
| 5,498,421 A | 3/1996 | Grinstaff et al. |
| 5,505,932 A | 4/1996 | Grinstaff et al. |
| 5,508,021 A | 4/1996 | Grinstaff et al. |
| 5,512,268 A | 4/1996 | Grinstaff et al. |
| 5,540,931 A | 7/1996 | Hewitt et al. |
| 5,560,933 A | 10/1996 | Soon-Shiong et al. |
| 5,635,207 A | 6/1997 | Grinstaff et al. |
| 5,639,473 A | 6/1997 | Grinstaff et al. |
| 5,650,156 A | 7/1997 | Grinstaff et al. |
| 5,665,382 A | 9/1997 | Grinstaff et al. |
| 5,665,383 A | 9/1997 | Grinstaff et al. |
| 5,916,596 A | 6/1999 | Desai et al. |
| 5,997,904 A | 12/1999 | Magdassi et al. |
| 6,096,331 A | 8/2000 | Desai et al. |
| 6,506,405 B1 | 1/2003 | Desai et al. |
| 6,528,067 B1 | 3/2003 | Magdassi et al. |
| 6,537,579 B1 | 3/2003 | Desai et al. |
| 6,652,884 B2 | 11/2003 | Falciani |
| 6,749,868 B1 | 6/2004 | Desai et al. |
| 6,753,006 B1 | 6/2004 | Desai et al. |
| 7,771,751 B2 | 8/2010 | Desai et al. |
| 7,820,788 B2 | 10/2010 | Desai et al. |
| 7,923,536 B2 | 4/2011 | Desai et al. |
| 7,981,445 B2 | 7/2011 | De et al. |
| 8,034,375 B2 | 10/2011 | Desai et al. |
| 8,034,765 B2 | 10/2011 | De et al. |
| 8,137,684 B2 | 3/2012 | Desai et al. |
| 8,138,229 B2 | 3/2012 | Desai et al. |
| 8,257,733 B2 | 9/2012 | Desai et al. |
| 8,268,348 B2 | 9/2012 | Desai et al. |
| 8,314,156 B2 | 11/2012 | Desai et al. |
| 8,735,394 B2 | 5/2014 | Desai et al. |
| 2003/0054042 A1 | 3/2003 | Liversidge et al. |
| 2003/0199425 A1 | 10/2003 | Desai et al. |
| 2004/0126400 A1 | 7/2004 | Iverson et al. |
| 2005/0004002 A1 | 1/2005 | Desai et al. |
| 2005/0038498 A1 | 2/2005 | Dubrow et al. |
| 2005/0119330 A1 | 6/2005 | Kao et al. |
| 2005/0152979 A1 | 7/2005 | Besman et al. |
| 2005/0203013 A1 | 9/2005 | Soker et al. |
| 2005/0209266 A1 | 9/2005 | Garvey |
| 2005/0244339 A1 | 11/2005 | Jauernigh et al. |
| 2006/0073182 A1 | 4/2006 | Wong et al. |
| 2006/0210638 A1 | 9/2006 | Liversidge et al. |
| 2006/0263434 A1 | 11/2006 | Desai et al. |
| 2007/0066522 A1 | 3/2007 | McCormick et al. |
| 2007/0082838 A1 | 4/2007 | De et al. |
| 2007/0087022 A1 | 4/2007 | Desai et al. |
| 2007/0092563 A1 | 4/2007 | Desai et al. |
| 2007/0093547 A1 | 4/2007 | Desai et al. |
| 2007/0116774 A1 | 5/2007 | Desai et al. |
| 2007/0129448 A1 | 6/2007 | Desai et al. |
| 2007/0166388 A1 | 7/2007 | Desai et al. |
| 2008/0063724 A1 | 3/2008 | Desai et al. |
| 2008/0153738 A1 | 6/2008 | Desai et al. |
| 2008/0161382 A1 | 7/2008 | Desai et al. |
| 2008/0213370 A1 | 9/2008 | Desai et al. |
| 2008/0280987 A1 | 11/2008 | Desai et al. |
| 2009/0098210 A1 | 4/2009 | Desai et al. |
| 2009/0175951 A1 | 7/2009 | Liversidge |
| 2009/0196933 A1 | 8/2009 | De et al. |
| 2009/0263483 A1 | 10/2009 | Desai et al. |
| 2009/0304805 A1 | 12/2009 | Desai et al. |
| 2010/0035800 A1 | 2/2010 | Desai et al. |
| 2010/0048499 A1 | 2/2010 | Desai et al. |
| 2010/0112077 A1 | 5/2010 | Desai et al. |
| 2010/0166869 A1 | 7/2010 | Desai et al. |
| 2010/0183728 A1 | 7/2010 | Desai et al. |
| 2010/0297243 A1 | 11/2010 | Desai et al. |
| 2011/0052708 A1 | 3/2011 | Soon-Shiong et al. |
| 2011/0064812 A1 | 3/2011 | Bahl et al. |
| 2012/0070502 A1 | 3/2012 | Desai et al. |
| 2012/0076862 A1 | 3/2012 | Desai et al. |
| 2012/0128732 A1 | 5/2012 | Trieu et al. |
| 2012/0189701 A1 | 7/2012 | Desai et al. |
| 2012/0231082 A1 | 9/2012 | Desai et al. |
| 2012/0283205 A1 | 11/2012 | Desai et al. |
| 2013/0045240 A1 | 2/2013 | Tao et al. |
| 2013/0071438 A1 | 3/2013 | Desai et al. |
| 2013/0115296 A1 | 5/2013 | Yeo et al. |
| 2013/0195922 A1 | 8/2013 | Desai et al. |
| 2013/0195983 A1 | 8/2013 | Desai et al. |
| 2013/0195984 A1 | 8/2013 | Desai et al. |
| 2013/0202709 A1 | 8/2013 | Desai et al. |
| 2013/0209518 A1 | 8/2013 | Desai et al. |
| 2013/0244952 A1 | 9/2013 | Desai et al. |
| 2013/0266659 A1 | 10/2013 | Desai et al. |
| 2013/0280336 A1 | 10/2013 | Desai et al. |
| 2013/0280337 A1 | 10/2013 | Desai et al. |
| 2014/0017315 A1 | 1/2014 | Desai et al. |
| 2014/0017316 A1 | 1/2014 | Desai et al. |
| 2014/0017323 A1 | 1/2014 | Desai et al. |
| 2014/0023717 A1 | 1/2014 | Desai et al. |
| 2014/0039069 A1 | 2/2014 | Desai et al. |
| 2014/0039070 A1 | 2/2014 | Desai et al. |
| 2014/0056986 A1 | 2/2014 | Desai et al. |
| 2014/0072630 A1 | 3/2014 | Tao et al. |
| 2014/0072631 A1 | 3/2014 | Trieu et al. |
| 2014/0072643 A1 | 3/2014 | Desai et al. |
| 2014/0079787 A1 | 3/2014 | Yeo et al. |
| 2014/0079788 A1 | 3/2014 | Desai et al. |
| 2014/0079793 A1 | 3/2014 | Desai et al. |
| 2014/0080901 A1 | 3/2014 | Desai et al. |
| 2014/0134257 A1 | 5/2014 | Desai et al. |
| 2014/0155344 A1 | 6/2014 | Desai et al. |
| 2014/0170228 A1 | 6/2014 | Desai et al. |
| 2014/0186447 A1 | 7/2014 | Desai |
| 2014/0199403 A1 | 7/2014 | Desai et al. |
| 2014/0199404 A1 | 7/2014 | Heise et al. |
| 2014/0199405 A1 | 7/2014 | Pierce et al. |

FOREIGN PATENT DOCUMENTS

| | | |
|---|---|---|
| WO | WO-94/18954 A1 | 9/1994 |
| WO | WO-98/14174 A1 | 4/1998 |
| WO | WO-98/14175 A1 | 4/1998 |
| WO | WO-99/00113 A1 | 1/1999 |
| WO | WO-00/64437 A1 | 11/2000 |
| WO | WO-00/71079 A2 | 11/2000 |
| WO | WO-00/71079 A3 | 11/2000 |
| WO | WO-01/89522 A1 | 11/2001 |
| WO | WO-02/080975 A1 | 10/2002 |
| WO | WO-02/087545 A1 | 11/2002 |
| WO | WO-03/096944 A1 | 11/2003 |
| WO | WO-2004/052401 A2 | 6/2004 |
| WO | WO-2004-052401 A3 | 6/2004 |
| WO | WO-2005/117952 A2 | 12/2005 |
| WO | WO-2005/117952 A3 | 12/2005 |
| WO | WO-2006/053754 A1 | 5/2006 |
| WO | WO-2006/089207 A2 | 8/2006 |
| WO | WO-2006-089207 A3 | 8/2006 |
| WO | WO-2006/089290 A1 | 8/2006 |
| WO | WO-2006/124739 A1 | 11/2006 |
| WO | WO-2007/027819 A2 | 3/2007 |
| WO | WO-2007/027941 A2 | 3/2007 |
| WO | WO-2007/027941 A3 | 3/2007 |
| WO | WO-2008/027055 A1 | 3/2008 |
| WO | WO-2008/057562 A1 | 5/2008 |
| WO | WO-2008/076373 A1 | 6/2008 |
| WO | WO-2008/109163 A1 | 9/2008 |
| WO | WO-2008/137148 A2 | 11/2008 |
| WO | WO-2008-137148 A3 | 11/2008 |
| WO | WO-2008/150532 A1 | 12/2008 |

OTHER PUBLICATIONS

West, "Abraxane Bests Taxol in Response Rate for NSCLC: What Might this Mean?" www.cancerGRACE.org, Mar. 20, 2010, pp. 1-3.*

Kita et al, "The effect of single weekly paclitaxel in heavily pretreated patients with recurrent or persistent advanced ovarian cancer," Gynecologic Oncology 92, 2004, pp. 813-818.*

(56) References Cited

OTHER PUBLICATIONS

European Office Action mailed on Jun. 30, 2011, for European Patent Application No. 08 768 111.0 filed on Jun. 2, 2008, 5 pages.
U.S. Appl. No. 13/228,323, filed Sep. 8, 2011, for Desai et al.
U.S. Appl. No. 13/263,723, internationally filed Apr. 9, 2010, for Desai et al.
U.S. Appl. No. 13/133,367, internationally filed Dec. 11, 2009, for Trieu et al.
U.S. Appl. No. 13/255,893, internationally filed Mar. 12, 2010, for Desai et al.
U.S. Appl. No. 13/073,824, filed Mar. 28, 2011, for Desai et al.
U.S. Appl. No. 13/073,861, filed Mar. 28, 2011, for Desai et al.
U.S. Appl. No. 13/368,250, filed Feb. 7, 2012, for Desai et al.
U.S. Appl. No. 13/368,297, filed Feb. 7, 2012, for Desai et al.
Adnot, S. et al. (Jan. 1991). "Loss of Endothelium-Dependent Relaxant Activity in the Pulmonary Circulation of Rats Exposed to Chronic Hypoxia," *J. Clin. Invest.* 87(1):155-162.
Al Housseini, A et al. (Mar. 1, 2008). "A Phase II, Non-Randomized Study of Abraxane plus Carboplatin in Patients With Recurrent Platinum-Sensitive Ovarian or Primary Peritoneal Cancer: Evaluation of the Response and Survival and Progression-Free Survival," *Gynecologic Oncology*, 108(Suppl. 1): S129-S130, Abstract No. 293.
Carmeliet, P. et al. (Sep. 14, 2000). "Angiogenesis in Cancer and Other Diseases," *Nature* 407(6801):249-257.
Carter, D. C. et al. (1994). "Structure of Serum Albumin," *Adv. Protein. Chem.* 45:153-203.
Chauhan, D. et al. (Feb. 1, 1996). "Multiple Myeloma Cell Adhesion-Induced Interleukin-6 Express in Bone Marrow Stromal Cells Involves Activation of NF-Kappa B," *Blood* 87(3):1104-1112.
Curry, S. et al. (Sep. 1998). "Crystal Structure of Human Serum Albumin Complexed with Fatty Acid Reveals an Asymmetric Distribution of Binding Sites," *Nat. Struct. Biol.* 5(9):827-835.
Curry, S. et al. (1999). "Fatty Acid Binding to Human Serum Albumin: New Insights from Crystallographic Studies," *Biochim. Biophys. Acta* 1441:131-140.
De Tapas, K. et al. (Apr. 17, 2007) "Nanoparticle Albumin-Bound (*nab*) Rapamycin as an Anticancer Agent," *Proceedings of the Annual Meeting of the American Association for Cancer Research*, held on Apr. 14, 18, 2007, in Los Angeles, California 48(1):1117, Abstract No. 4719.
Ellerby, H. M. et al. (Sep. 1999). "Anti-Cancer Activity of Targeted Pro-Apoptotic Peptides," *Nat. Med.* 5(9):1032-1038.
Fehske, K. J. et al. (Apr. 1, 1981). "The Location of Drug Binding Sites in Human Serum Albumin," *Biochem. Pharmacol.* 30(7):687-692.
Gartner, S. et al. (Aug. 1980). "Long-Term Culture of Human Bone Marrow Cells," *Proc. Natl. Acad. Sci. USA* 77(8):4756-4759.
Gupta, D. et al. (Dec. 2001). "Adherence of Multiple Myeloma Cells to Bone Marrow Stromal Cells Upregulates Vascular Endothelial Growth Factor Secretion: Therapeutic Applications," *Leukemia* 15(12):1950-1961.
Hawkins, M. J. et al. (May 22, 2008, e-pub. Feb. 7, 2008). "Protein Nanoparticles as Drug Carriers in Clinical Medicine," *Advanced Drug Delivery Reviews* 60(8):876-885.
He, X. M. et al. (Jul. 16, 1992). "Atomic Structure and Chemistry of Human Serum Albumin," *Nature* 358(6383):209-215.
Herzog, T. J. (Nov. 15, 2004). "Recurrent Ovarian Cancer: How Important is it to Treat to Disease Progression?" *Clin. Cancer Res.* 10:7439-7449.
Icon et al. (Jun. 21, 2003). "Paclitaxel Plus Platinum-Based Chemotherapy Versus Conventional Platinum-Based Chemotherapy in Women with Relapsed Ovarian Cancer: The ICON4/AGO-OVAR-2.2 Trial," *Lancet* 361(9375):2099-2106.
Koshkina, N. V. et al. (2003). "Camptothecins and Lung Cancer: Improved Delivery Systems by Aerosol," *Current Cancer Drug Targets* 3(4):251-264.
Kragh-Hansen, U. (Feb. 1990). "Structure and Ligand Binding Properties of Human Serum Albumin," *Dan. Med. Bull.* 37(1)57-84.

Micha, J. P. et al. (Feb. 2006, e-pub. Oct. 15, 2005). "Abraxane in the Treatment of Ovarian Cancer: The Absence of Hypersensitivity Reactions," *Gynecologic Oncology* 100(2):437-438.
Mitsiades, C. S. et al. (Aug. 1, 2001). "Trail/Apo2L Ligand Selectively Induces Apoptosis and Overcomes Drug Resistance in Multiple Myeloma: Therapeutic Applications," *Blood* 98(3):795-804.
Mitsiades, N. et al. (Oct. 29, 2002). "Molecular Sequelae of Proteasome Inhibition in Human Multiple Myeloma Cells," *Proc. Natl. Acad. Sci. USA* 99(22):14374-14379.
Mitsiades, N. et al. (May 15, 2003). "Molecular Sequelae of Histone Deacetylase Inhibition in Human Malignant B Cells," *Blood* 101(10):4055-4062.
Mitsiades, N. et al. (Mar. 15, 2003). "The Proteasome Inhibitor PS-341 Potentiates Sensitivity of Multiple Myeloma Cells to Conventional Chemotherapeutic Agents: Therapeutic Applications," *Blood* 101(6):2377-2380.
Muggia, F. M. (Dec. 2006). "New and Emerging Intraperitoneal (IP) Drugs for Ovarian Cancer Treatment," *Seminars in Oncology* 33(6)(Suppl. 12):S18-S24.
Nishimura. T. et al. (Feb. 2001). "40-*O*-(2-Hydroxyethyl)-rapamycin Attenuates Pulmonary Arterial Hypertension and Neointimal Formation in Rats," *Am. J. Respir. Crit. Care Med.* 163(2):498-502.
Paddenberg, R. et al. (Feb. 24, 2007). "Rapamycin Attenuates Hypoxia-Induced Pulmonary Vascular Remodeling and Right Ventricular Hypertrophy in Mice," *Respiratory Research* 8(1):15, total of 12 pages.
Rustin, G. J. et al. (Jun. 1, 2004). "Use of CA-125 in Clinical Trial Evaluation of New Therapeutic Drugs for Ovarian Cancer," *Clin. Cancer Res.* 10(11):3919-3926.
Sugio, S. et al. (Jun. 1999). "Crystal Structure of Human Serum Albumin at 2.5 Å Resolution," *Protein. Eng.* 12(6):439-446.
Tai, Y.-T. et al. (Feb. 21, 2000). "Isolation and Characterization of Human Multiple Myeloma Cell Enriched Populations," *J. Immunol. Methods* 235(1-2):11-19.
Therasse, P. et al. (Feb. 2, 2000). "New Guidelines to Evaluate the Response to Treatment in Solid Tumors," *J. Natl. Cancer Inst.* 92(3):205-216.
Trieu, V. et al. (Dec. 2007). "mTOR Inhibitor Nanoparticle Albumin-Bound (nab) Rapamycin is Effective in a Breast Cancer Xenograft Model," *Breast Cancer Research and Treatment, 30th Annual San Antonio Breast Cancer Symposium;* San Antonio, Texas, USA, held on Dec. 13-16, 2007 106(supplement 1):5268, Abstract 6063.
Uchiyama, H. et al. (Dec. 15, 1993). "Adhesion of Human Myeloma-Derived Cell Lines to Bone Marrow Stromal Cells Stimulates Interleukin-6 Secretion," *Blood* 82(12):3712-3720.
Vorum, H. (Nov. 1999). "Reversible Ligand Binding to Human Serum Albumin. Theoretical and Clinical Aspects," *Dan. Med. Bull.* 46(5):379-399.
Zaiman, A. et al. (Nov. 2005). "One Hundred Years of Research in the Pathogenesis of Pulmonary Hypertension," *Am. J. Respir. Cell Mol. Biol.* 33(5):425-431.
Zhou, H. al. (Jan. 2006). "Heme Oxygenase-1 Mediates the Protective Effects of Rapamycin in Monocrotaline-Induced Pulmonary Hypertension," *Lab. Investigation* 86(1):62-71.
International Search Report mailed on Jul. 22, 2008, for PCT Patent Application No. PCT/US2008/003096 filed on Mar. 7, 2008, published as WO 2008/109163 on Sep. 12, 2008, 3 pages.
Written Opinion mailed on Jul. 22, 2008, for PCT Patent Application No. PCT/US2008/003096 filed on Mar. 7, 2008, published as WO 2008/109163 on Sep. 12, 2008, 10 pages.
International Search Report mailed on Dec. 22, 2008, for PCT Patent Application No. PCT/US2008/005792 filed on May 5, 2008, published as WO 2008/137148 on Nov. 13, 2008, 7 pages.
Written Opinion mailed on Dec. 22, 2008, for PCT Patent Application No. PCT/US2008/005792 filed on May 5, 2008, published as WO 2008/150531 on Nov. 13, 2008, 10 pages.
International Search Report mailed on Oct. 9, 2008, for PCT Patent Application No. PCT/US2008/007024 filed on Jun. 2, 2008, published as WO 2008/150532 on Dec. 11, 2008, 3 pages.
Written Opinion mailed on Oct. 9, 2008, for PCT Patent Application No. PCT/US2008/007024 filed on Jun. 2, 2008, published as WO 2008/150532 on Dec. 11, 2008, 6 pages.
U.S. Appl. No. 09/937,840, filed Jan. 28, 2002, for Desai et al.

(56) References Cited

OTHER PUBLICATIONS

U.S. Appl. No. 12/479,710, filed Jun. 5, 2009, for Desai et al.
U.S. Appl. No. 12/818,099, filed Jun. 17, 2010 for De et al.
U.S. Appl. No. 12/824,014, filed Jun. 25, 2010 for Desai et al.
U.S. Appl. No. 12/874,965, filed Sep. 2, 2010, for De et al.
U.S. Appl. No. 12/832,876, filed Jul. 8, 2010, for Desai et al.
U.S. Appl. No. 12/910,693, filed Oct. 22, 1010, for Desai et al.
U.S. Appl. No. 13/038,287, filed Mar. 1, 2011, for Desai et al.
Hideshima, T. et al. (May 15, 2006). "Perifosine, An Oral Bioactive Novel Alkylphospholipid, Inhibits Akt and Induces in Vitro and in Vivo Cytotoxicity in Human Multiple Myeloma Cells," *Blood* 107(10):4053-4062.
De Mulder, P.H. et al. (2004). "Current Treatment of Renal Cell Carcinoma," *Ann. Oncol.* 15(Suppl. 4):319-328.
Muramatsu, T. et al. (Jul. 1, 2006). "Treatment Strategy for Recurrent and Refractory Epithelial Ovarian Cancer: Efficacy of High-Dose Chemotherapy With Hematopoietic Stem Cell Transplantation," *Acta Histochem. Cytochem.* 39(3):61-67.
European Office Action mailed on Jul. 5, 2012, for European Patent Application No. 08768111.0 filed on Jun. 2, 2008, 3 pages.
U.S. Appl. No. 09/446,783, filed May 16, 2000, for Desai et al.
U.S. Appl. No. 13/408,994, filed Feb. 29, 2012, for De et al.
Ballou, L. M. et al. (Jun. 27, 2003). "Activated $G\alpha_q$ Inhibits p110$\alpha$ Phosphatidylinositol 3-Kinase and Akt," *J. Biol. Chem.* 278(26)23472-23479.
Beppo, M. et al. (May 2001). "Weekly Paciltaxel and Cisplatin in Recurrent Ovarian Cancer," *Japanese Journal of Cancer and Chemotherapy* 28(50):643-648. (English Abstract).
Gonzalez-Martin, A.J. et al. (2005). "Randomized Phase II Trial of Carbplatin Versus Paclitaxel and Carboplatin in Platinum-Sensitive Recurent Advanced Ovarian Carcinoma: A GEICO (Grupo Espanol de Investigacion en Cancer de Ovario) Study," *Annals of Oncology* 16(5):749-755.
Kawagoe, H. et al. (Jan. 2003). "Weekly Paclitaxel Infusion in Patients with Recurrent Ovarian Cancer—A Pilot Study," *Japanese Journal of Cancer and Chemotherapy* 30(1):151-154. (English Abstract).
Rose, P.G. et al. (1998). "Second-Line Therapy With Paclitaxel and Carboplatin for recurrent Disease Following First-Line Therapy With Paclitaxel and Platinum in Ovarian or Peritoneal Carcinoma," *Journal of Clinical Oncology* 16(4):1494-1497.
Sarbassov, D. D. et al. (Apr. 21, 2006). "Prolonged Rapamycin Treatment Inhibits mTORC2 Assembly and Akt/PKB," *Mol. Cell.* 22(2):159-168.
Uraba, S. et al. (Mar. 2004). "Recurrent Ovarian Cancer Peitonitis Treated with Weekly Paclitaxel Infusion: A clinicopharmological Study," *Japanese Journal of Cancer and Chemotherapy* 31(3):449-451. (English Abstract).
European Search Report mailed on Sep. 7, 2012, for European Patent Application No. 12152463.1, filed on Mar. 7, 2008, published on Aug. 1, 2012, as EP 2 481 409, 8 pages.
European Search Report mailed on Sep. 11, 2012, for European Patent Application No. 08767585.6, filed on Mar. 5, 2008, published on Jan. 27, 2010, as EP 2 146 707, 4 pages.
European Office Action mailed on Sep. 4, 2012, for European Patent Application No. 08726605.2 filed on Mar. 7, 2008, 7 pages.
European Search Report and European Search Opinion mailed on Sep. 17, 2012, for European Patent Application No. 12152455.7, filed on Mar. 7, 2008, published on Aug. 1, 2012, as EP 2 481 402, 9 pages.
U.S. Appl. No. 13/649,987, filed Oct. 11, 2012, for Desai et al.
U.S. Appl. No. 13/777,980, filed Feb. 26, 2013, for Desai et al.
U.S. Appl. No. 13/777,988, filed Feb. 26, 2013, for Desai et al.
U.S. Appl. No. 13/564,633, filed Aug. 1, 2012, for Desai et al.
U.S. Appl. No. 13/585,696, filed Aug. 14, 2012, for Desai et al.
U.S. Appl. No. 13/743,212, filed Jan. 1, 2013, for Desai et al.
U.S. Appl. No. 13/776,481, filed Feb. 25, 2013, for Desai et al.
U.S. Appl. No. 13/776,484, filed Feb. 25, 2013, for Desai et al.
U.S. Appl. No. 13/779,625, filed Feb. 27, 2013, for Desai et al.
U.S. Appl. No. 13/779,624, filed Feb. 27, 2013, for Desai et al.
U.S. Appl. No. 13/779,621, filed Feb. 27, 2013, for Desai et al.
U.S. Appl. No. 13/781,482, filed Feb. 28, 2013, for Desai et al.
U.S. Appl. No. 13/392,501, internationally filed Aug. 25, 2010, for Tao et al.
U.S. Appl. No. 13/423,095, filed Mar. 16, 2012, for Desai et al.
U.S. Appl. No. 13/781,479, filed Feb. 28, 2013, for Desai et al.
U.S. Appl. No. 13/781,489, filed Feb. 28, 2013, for Trieu et al.
U.S. Appl. No. 13/781,487, filed Feb. 28, 2013, for Tao et al.
U.S. Appl. No. 13/585,603, internationally filed Mar. 25, 2011, for Yeo et al.
U.S. Appl. No. 13/781,480, filed Feb. 28, 2013, for Yeo et al.
U.S. Appl. No. 13/782,990, filed Mar. 1, 2013, for Desai et al.
U.S. Appl. No. 13/782,988, filed Mar. 1, 2013, for Desai et al.
U.S. Appl. No. 13/701,003, filed May 20, 2011, for Desai et al.
U.S. Appl. No. 13/782,984, filed Mar. 1, 2013, for Desai et al.
U.S. Appl. No. 13/701,002, filed May 20, 2011, for Desai et al.
U.S. Appl. No. 13/783,122, filed Mar. 1, 2013, for Desai et al.
U.S. Appl. No. 13/701,001, filed May 20, 2011, for Desai et al.
U.S. Appl. No. 13/782,992, filed Mar. 1, 2013, for Desai et al.
U.S. Appl. No. 13/794,705, filed Mar. 12, 2013, for Desai et al.
U.S. Appl. No. 13/791,841, filed Mar. 12, 2013, for Desai et al.
U.S. Appl. No. 13/794,480, filed Mar. 12, 2013, for Desai et al.
U.S. Appl. No. 13/794,486, filed Mar. 12, 2013, for Heise et al.
U.S. Appl. No. 13/794,712, filed Mar. 11, 2013, for Pierce et al.
Aapro, M. et al. (Apr. 2014). "Adverse Event Management in Patients With Advanced Cancer Receiving Oral Everolimus: Focus on Breast Cancer," *Annals of Oncology* 25(4):763-773.
Afinitor® Insert. (Feb. 2014). "Highlights of Prescribing Information," Afinitor® pp. 1-41.
Amato, R. J. et al. (Jun. 1, 2009, e-pub. Mar. 20, 2009). "A Phase 2 Study With a Daily Regimen of the Oral mTOR Inhibitior RAD001 (Everolimus) in Patients With Metastatic Clear Cell Renal Cell Cancer," *Cancer* 115:2438-2446.
Atkins, M.B. et al. (Mar. 1, 2004). "Radomized Phase II Study of Multiple Dose Levels of CCI-779, a Novel Mammalian Target of Rapamycin Kinase Inhibitor, in Patients With Advanced Refractory Renal Cell Carcinoma," *Journal of Clinical Oncology* 22(5):909-918.
Baselga, J. et al. (Jun. 1, 2009, e-pub. Jan. 12, 2009). "Phase II Randomized Study of Neoadjuvant Everolimus Plus Letrozole Compared With Placebo Plus Letrozole in Patients With Estrogen Receptor-Positive Breast Cancer," *Journal of Clinical Oncology* 27(16):2630-2637.
Baselga, J. et al. (Feb. 9, 2012, e-pub. Dec. 7, 2011). "Everolimus in Postmenopausal Hormone-Receptor-Positive Advanced Breast Cancer," *The New England Journal of Medicine* 366(6):520-529.
Bryce, A.H. et al. (Oct. 2012). "Phase I Study of Temsirolimus in Combination With EKB-569 in Patients With Advanced Solid Tumors," *Invest New Drugs* 30(5):1-16.
Buckner, J.C. et al. (2010, e-pub. May 5, 2009). "Phase I, Pharmacokinetic Study of Temsirolimus Administered Orally to Patients With Advanced Cancer," *Invest New Drugs* 28:334-342.
Campone, M. et al. (2009, e-pub. Jan. 6, 2009). "Safety and Pharmacokinetics of Paclitaxel and the Oral mTOR Inhibitor Everolimus in Advanced Solid Tumuors," *British Journal of Cancer* 100(2):315-321.
Chan, S. et al. (Aug. 10, 2005). "Phase II Study of Temsirolimus (CCI-779), A Novel Inhibitor of mTOR, in Heavily Pretreated Patients With Locally Advanced or Metastatic Breast Cancer," *Journal of Clinical Oncology* 23(23):5314-5322.
Chawla, S.P. et al. (Jan. 1, 2012, e-pub. Nov. 7, 2011). "Phase II Study of the Mammalian Target of Rapamycin Inhibitor Ridaforolimus in Patients With Advanced Bone and Soft Tissue Sarcomas," *Journal of Clinical Oncology* 30(1):78-84.
Cohen, E.E.W. et al. (Sep. 1, 2012, e-pub. Aug. 7, 2012). "Phase I Studies of Sirolimus Alone or in Combination With Pharmacokinetic Modulators in Advanced Cancer Patients," *Clin. Cancer Res.* 18(17):4785-4793.
Deenen, M.J. et al. (2012, e-pub. Aug. 2, 2011). "Phase I and Pharmacokinetic Study of Capecitabine and the Oral mTOR Inhibitor Everolimus in Patients with Advanced Solid Malignancies," *Invest New Drugs* 30:1557-1565.

(56) References Cited

OTHER PUBLICATIONS

Doi, T. et al. (Apr. 10, 2010, e-pub. Mar. 15, 2010). "Multicenter Phase II Study of Everolimus in Patients With Previously Treated Metastatic Gastric Cancer," *Journal of Clinical Oncology* 28(11):1904-1910.
Duran, I. et al. (2006, e-pub. Oct. 10, 2006). "A Phase II Clinical and Pharmacodynamic Study of Temsirolimus in Advanced Neuroendocrine Carcinomas," *British Journal of Cancer* 95(9):1148-1154.
Ellard, S.L. et al. (Sep. 20, 2009, e-pub. Aug. 17, 2009). "Randomized Phase II Study Comparing Two Schedules of Everolimus in Patients With Recurrent/Metastatic Breast Cancer: NCIC Clinical Trials Group IND. 163," *Journal of Clinical Oncology* 27(27):4536-4541.
Farag, S.S. et al. (Nov. 2009). "Phase II Trial of Temsirolimus in Patients with Relapsed or Refractory Multiple Myeloma," *Leuk. Res.* 33(11):1475-1480.
Fouladi, M. et al. (Oct. 20, 2007). "Phase I Study of Everolimus in Pediatric Patients With Refractory Solid Tumors," *Journal of Clinical Oncology* 25(30):4806-4812.
Fujisaka, Y. et al. (2010, e-pub. Apr. 29, 2010). "A Phase 1 Clinical Study of Temsirolimus (CCI-779) in Japanese Patients With Advanced Solid Tumor," *Jpn. J. Clin. Oncol.* 40(8):732-738.
Galanis, E. et al. (Aug. 10, 2005). "Phase II Trial of Temsirolimus (CCI-779) in Recurrent Glioblastoma Multiforme: A North Central Cancer Treatment Group Study," *Journal of Clinical Oncology* 23(23):5294-5304.
Gonzalez-Angulo, A.M. et al. (Oct. 1, 2013). "Weekly *nab*-Rapamycin in Patients With Advanced Nonhematologic Malignancies: Final Results of a Phase I Trial," *Clinical Cancer Research* 19(19):5474-5484.
Hainsworth, J.D. et al. (May 1, 2010, e-pub. Apr. 5, 2010). "Phase II Trial of Bevacizumab and Everolimus in Patients With Advanced Renal Cell Carcinoma," *Journal of Clinical Oncology* 28(13):2131-2136.
Hartford, C.M. et al. (Feb. 15, 2009). "A Phase I Trial to Determine the Safety, Tolerability, and Maximum Tolerated Dose of Deforolimus in Patients With Advanced Malignancies," *Clin. Cancer Res.* 15(4):1428-1434.
Hess, G. et al. (Aug. 10, 2009, e-pub. Jul. 6, 2009). "Phase III Study to Evaluate Temsirolimus Compared With Investigator's Choice Therapy for the Treatment of Relapsed or Refractory Mantle Cell Lymphoma," *Journal of Clinical Oncology* 27(23):3822-2829.
Hidalgo, M. et al. (Oct. 1, 2006). "A Phase I and Pharmacokinetic Study of Temsirolimus (CCI-779) Administered Intravenously Daily for 5 Days Every 2 Weeks to Patients With Advanced Cancer," *Clin. Cancer Res.* 12(19):5755-5763.
Hudes, G. et al. (May 31, 2007). "Temsirolimus, Interferon Alfa, or Both for Advanced Renal-Cell Carcinoma," *The New England Journal of Medicine* 356(22):2271-2281.
Javle, M.M. et al. (2010). "Inhibition of the Mammalian Target of Rapamycin (mTOR) in Advanced Pancreatic Cancer: Results of Two Phase II Studies," *BMC Cancer* 10(368)1-7.
Margolin, K. et al. (Sep. 1, 2005, e-pub. Jul. 8, 2005). "CCI-779 in Metastatic Melanoma. A Phase II Trial of the California Cancer Consortium," *Cancer* 104(5):1045-1048.
Martins, F. et al. (2013, e-pub. Jan. 9, 2013). "A Review of Oral Toxicity Associated With mTOR Inhibitor Therapy in Cancer Patients," *Oral Oncology* 49:293-298.
Meier-Kriesche, H-U. et al. (2000). "Toxicity and Efficacy of Sirolimus: Relationship to Whole-Blood Concentrations," *Clinical Therapeutics* 22(Suppl. B):B93-B100.
Milton, D.T. et al. (Aug. 1, 2007, e-pub. Jun. 18, 2007). "Phase 1 Trial of Everolimus and Gefitinib in Patients With Advanced Nonsmall-Cell Lung Cancer," *Cancer* 110(3):599-605.
Mita, M.M. et al. (Jan. 20, 2008). "Phase I Trial of the Novel Mammalian Target of Rapamycin Inhibitor Deforolimus (AP23573; MK-8669) Administered Intravenously Daily for 5 Days Every 2 Weeks to Patients With Advanced Malignancies," *Journal of Clinical Oncology* 26(3):361-367.

Motzer, R.J. et al. (Sep. 1, 2007). "Phase I/II Trial of Temsirolimus Combined With Interferon Alfa for Advanced Renal Cell Carcinoma," *Journal of Clinical Oncology* 25(25):3958-3964.
Motzer, R.J. et al. (Sep. 15, 2010, e-pub. Jun. 14, 2010). "Phase 3 Trial of Everolimus for Metastatic Renal Cell Carcinoma," *Cancer* 116:4256-4265.
Naing, A. et al. (Sep. 15, 2011, e-pub. Jul. 12, 2011). "Phase I Trial of Cixutumumab Combined With Temsirolimus in Patients With Advanced Cancer," *Clin. Cancer Res.* 17(18):6052-6060.
O'Donnell, A. et al. (Apr. 1, 2008, e-pub. Mar. 10, 2008). "Phase I Pharmacokinetic and Pharmacodynamic Study of the Oral Mammalian Target of Rapamycin Inhibitior Everolimus in Patients With Advanced Solid Tumors," *Journal of Clinical Oncology* 26(10):1588-1595.
Okuno, S. et al. (Aug. 1, 2011, e-pub. Feb. 1, 2011). A Phase 2 Study of Temsirolimus (CCI-779) in Patients With Soft Tissue Sarcomas, *Cancer* 117:3468-3475.
Perotti, A. et al. (Oct. 20, 2010, e-pub. Sep. 20, 2010). "Phase IB Study of the mTOR Inhibitor Ridaforolimus With Capecitabine," *Journal of Clinical Oncology* 28(30):4554-4561.
Pfizer. (2012). Patient Information Leaflet included with Rapamune® (Sirolimus) Oral Solution and Tablets Packages Insert LAB-0579-1.0, instructions approved by the U.S. Food and Drug Administration, published under "Full Prescribing Information," at http://labeling.pfizer.com/showlabeling.aspx?id=139, instructions revised Dec. 2012 by Pfizer distributed by Wyeth Pharmaceuticals, Inc., 53 pages.
Pham, P-T.T. et al. (Apr. 27, 2004). "Sirolimus-Associated Pulmonary Toxicity," *Transplantation* 77(8):1215-1220.
Quek, R. et al. (Feb. 15, 2011, e-pub. Dec. 22, 2010). "Combination mTOR and IGF-1R Inhibition: Phase I Trial of Everolimus and Figitumumab in Patients With Advanced Sarcomas and Other Solid Tumors," *Clin. Cancer Res.* 17(4):871-879.
Raymond, E. et al. (Jun. 15, 2004). "Safety and Pharmacokinetics of Escalated Doses of Weekly Intravenous Infusion of CCI-779, A Novel mTOR Inhibitor, in Patients With Cancer," *Journal of Clinical Oncology* 22(12):2336-2347.
Rizzieri, D.A. et al. (May 1, 2008). "A Phase 2 Clinical Trial of Deforolimus (AP23573, MK-8669), A Novel Mammalian Target of Rapamycin Inhibitor, in Patients With Relapsed or Refractory Hematologic Malignancies," *Clin. Cancer Res.* 14(9):2756-2762.
Seront, E. et al. (Oct. 2012, e-pub. Apr. 3, 2012). "Phase II Study of Everolimus in Patients With Locally Advanced or Metastatic Transitional Cell Carcinoma of the Urothelial Tract: Clinical Activity, Molecular Response, and Biomarkers," *Annals of Oncology* 23(10):2663-2670.
Sessa, C. et al. (Jun. 2010, e-pub. Nov. 9, 2009). "Phase lb Study of Weekly Mammalian Target of Rapamycin Inhibitor Ridaforolimus (AP23573; MK-8669) With Weekly Paclitaxel," *Annals of Oncology* 21(6):1315-1322.
Slomovitz, B.M. et al. (Dec. 1, 2010, e-pub. Aug. 2, 2010). "A Phase 2 Study of the Oral Mammalian Target of Rapamycin Inhibitor, Everolimus, in Patients With Recurrent Endometrial Carcinoma," *Cancer* 116:5415-5419.
Sivendran, S. et al. (2014). "Metabolic Complications With the Use of mTOR Inhibitors for Cancer Therapy," *Cancer Treatment Reviews* 40:190-196.
Smith, S.M. et al. (Nov. 1, 2010, e-pub. Sep. 13, 2010). "Temsirolimus Has Activity in Non-Mantle Cell Non-Hodgkin's Lymphoma Subtypes: The University of Chicago Phase II Consortium," *Journal of Clinical Oncology* 28(31):4740-4746.
Soria, J-C. et al. (Oct. 2009, e-pub. Jun. 23, 2009). "Efficacy of Everolimus (RAD001) in Patients With Advanced NSCLC Previously Treated With Chemotherapy Alone or With Chemotherapy and EGFR Inhibitors," *Annals of Oncology* 20(10):1674-1681.
Tabernero, J. et al. (Apr. 1, 2008, e-pub. Mar. 10, 2008). "Dose- and Schedule-Dependent Inhibition of the Mammalian Target of Rapamycin Pathway With Everolimus: A Phase I Tumor Pharmacodynamic Study in Patients With Advanced Solid Tumors," *Journal of Clinical Oncology* 28(10):1603-1610.
Tarhini, A. et al. (Dec. 1, 2010, e-pub. Nov. 2, 2010). "Phase II Study of Everolimus (RAD001) in Previously Treated Small Cell Lung Cancer," *Clin. Cancer Res.* 16(23):5900-5907.

(56) References Cited

OTHER PUBLICATIONS

Torisel®, (May 2014). "Highlights of Prescribing Information," located at <http://labeling.pfizer.com/showlabeling.aspx?id=490>, last visited on May 15, 2014, 21 pages.

Witzig, T.E. et al. (Aug. 10, 2005). "Phase II Trial of Single-Agent Temsirolimus (CCI-779) for Relapsed Mantle Cell Lymphoma," *Journal of Clinical Oncology* 23(23):5347-5356.

Wolpin, B.M. et al. (Jan. 10, 2009, e-pub. Dec. 1, 2008). "Oral mTOR Inhibitor Everolimus in Patients With Gemcitabine-Refractory Metastatic Pancreatic Cancer," *Journal of Clinical Oncology* 27(2):193-198.

Yao, J.C. et al. (Feb. 10, 2011). "Everolimus for Advanced Pancreatic Neuroendocrine Tumors," *New England Journal of Medicine* 364(6):514-523.

Yao, J.C. et al. (Jan. 1, 2010, e-pub. Nov. 23, 2009). "Daily Oral Everolimus Activity in Patients With Metastatic Pancreatic Neuroendocrine Tumors After Failure of Cytotoxic Chemotherapy: A Phase II Trial," *Journal of Clinical Oncology* 28(1):69-76.

Yee, K.W.L. et al. (Sep. 1, 2006). "Phase I/II Study of the Mammalian Target of Rapamycin Inhibitor Everolimus (RAD001) in Patients With Relapsed or Refractory Hematologic Malignancies," *Clin. Cancer Res.* 12(17):5165-5173.

European Examination Report mailed May 9, 2014, for EP Application No. 08767585.6, filed on May 5, 2008, 7 pages.

Non-Final Office Action mailed on Feb. 13, 2014, for U.S. Appl. No. 13/781,479, filed Feb. 28, 2013, 39 pages.

Noh, W-C. et al. (Feb. 1, 2004). "Determinants of Rapamycin Sensitivity in Breast Cancer Cells," *Clinical Cancer Research* 10:1013-1023.

Punt, C.J.A. et al. (2003). "Phase I and Pharmacokinetic Study of CCI-779, a Novel Cytostatic Cell-Cycle Inhibitor, in Combination With 5-Fluorouracil and Leucovorin in Patients With Advanced Solid Tumors," *Annals of Oncology* 14:931-937.

\* cited by examiner

METHODS AND COMPOSITIONS FOR TREATING RECURRENT CANCER

CROSS-REFERENCE TO RELATED APPLICATIONS

This application is a National Phase filing under 35 U.S.C. §371 of International Application No. PCT/US2008/007024 having an international filing date of Jun. 2, 2008, which claims the priority benefit to the U.S. Provisional Patent Application No. 60/932,750 filed on Jun. 1, 2007, the contents of which are incorporated by reference herein in their entirety.

TECHNICAL FIELD

The present invention relates to methods and compositions for the treatment of recurrent cancer, particularly recurrent ovarian cancer, comprising the administration of compositions comprising nanoparticles comprising taxane and a carrier protein (such as albumin).

BACKGROUND

Ovarian cancer forms in tissues of an ovary (one of a pair of female reproductive glands in which the ova, or eggs, are formed). Most ovarian cancers are either ovarian epithelial carcinomas (cancer that begins in the cells on the surface of the ovary) or malignant germ cell tumors (cancer that begins in egg cells). According to the National Cancer Institute, ovarian cancer is the seventh most common cancer, with an estimated 20,180 new cases in 2006, but is the fourth most deadly, with an estimated 15,310 deaths in 2006.

A possible genetic contribution to ovarian cancer risk is indicated by the increased incidence of this cancer among women with a family history, and by the observation of rare families in which multiple family members are affected with ovarian cancer, in a pattern compatible with autosomal dominant inheritance of cancer susceptibility. Formal studies of families (linkage analysis) have subsequently proven the existence of autosomal dominant predispositions to ovarian cancer and have led to the identification of several highly penetrant genes as the cause of inherited cancer risk in many cancer-prone families. Mutations in these genes are rare in the general population and are estimated to account for no more than 5% to 10% of ovarian cancer cases overall.

Although reproductive, demographic, and lifestyle factors affect risk of ovarian cancer, the single greatest ovarian cancer risk factor is a family history of the disease. A large meta-analysis of 15 published studies estimated an odds ratio (OR) of 3.1 for the risk of ovarian cancer associated with at least one first-degree relative with ovarian cancer.

Despite recent improvements, initial or first-line chemotherapy fails to produce a remission in more than 70% of patients with ovarian cancer. Furthermore, approximately 40-50% of the women who do achieve a remission after first-line chemotherapy will experience a recurrence of cancer within 3 years. Patients with recurrent ovarian, peritoneal, or fallopian tube cancer generally have a poor outcome with current therapies. There is a need for effective treatment method for patients with recurrent ovarian cancers. Preferably, the treatments overcome the shortcomings of current drug and transplant treatments, such as hypersensitivity reactions due to the solvent/surfactant in which drugs are dissolved.

Many anti-proliferative agents are dissolved in a solvent/surfactant which produces hypersensitivity reactions. Great efforts have been invested on the development of water soluble prodrugs and derivatives of anti-proliferative agents with higher hydrophilic groups to enhance water solubility and thus obviate the need for potentially toxic solvents/surfactants. Another approach to address the problem associated with the poor water solubility of anti-proliferative agents is the development of various formulations such as nanoparticles, oil-in-water emulsions, and liposomes. For example, Abraxane® is a nanoparticle composition of paclitaxel and albumin. Nanoparticle compositions of substantially poorly water soluble drugs and uses thereof have been disclosed, for example, in U.S. Pat. Nos. 5,916,596; 6,096,331; 6,749,868; and 6,537,579; U.S. Patent Appln. Pub. No. US20030199425; and PCT Application Pub. Nos. WO98/14174, WO99/00113, WO07/027,941 and WO07/027,819. Administration of Abraxane® to a patient with recurrent ovarian cancer is described in Mida et al., *Gynecologic Oncology*, 100:437-438 (2006).

The disclosures of all publications, patents, patent applications and published patent applications referred to herein are hereby incorporated herein by reference in their entirety.

BRIEF SUMMARY OF THE INVENTION

The present invention provides methods for the treatment of a recurrent cancer (such as a recurrent gynecological cancer) by administering a composition comprising nanoparticles comprising a taxane and a carrier protein (hereinafter referred to as "taxane nanoparticle composition"). In some embodiments, there is provided a method of treating a recurrent cancer (such as a recurrent gynecological cancer, for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin). In some embodiments, the recurrent cancer (such as a recurrent gynecological cancer, for example recurrent ovarian, peritoneal, or fallopian tube cancer) is platinum sensitive. In some embodiments, the recurrent cancer (such as a recurrent gynecological cancer, for example recurrent ovarian, peritoneal, or fallopian tube cancer) is platinum resistant. In some embodiments, the recurrent cancer is a recurrent lung cancer.

In some embodiments, the recurrent cancer is a recurrent gynecological cancer. In some embodiments, the recurrent gynecological cancer is a recurrent ovarian cancer (such as a recurrent epithelial ovarian cancer). In some embodiments, the recurrent gynecological cancer is a recurrent peritoneal cancer. In some embodiments, the recurrent gynecological cancer is a recurrent fallopian tube cancer (including for example papillary serous adenocarcinomas, sarcomas, and transitional cell carcinomas). Other recurrent gynecological cancers such as recurrent malignant mixed mullerian tumor and serous endo can also be treated.

In some embodiments, the individual is a woman who is about 40 to about 85 years old, including for example about 60 to about 70 years old. In some embodiments, the individual has an Eastern Cooperative Oncology Group (ECOG) performance status of 0-2 (such as any of 0, 1, or 2) prior to the administration of the taxane nanoparticle composition. In some embodiments, the individual has received a prior cancer therapy (such as chemotherapy) and has a treatment free interval for more than about any of 3, 6, or 9 months since the completion of prior chemotherapy. In some embodiments, the individual has received a prior cancer therapy (such as chemotherapy) and has a treatment free interval for more than about any of 12, 18, 24, 36, or 48 months since the completion of prior chemotherapy. In some embodiments, the prior chemotherapy has a different mechanism of action than that of the taxane. In some embodiments, the individual has only been treated with platinum-based agent(s) prior to the administration of the taxane nanoparticle composition. In some embodiments, the individual has only been treated with one dosing regime prior to the administration of the taxane nanoparticle composition. In some embodiments, the individual has not previously been treated with a taxane-based therapy.

In some embodiments, the individual has received a prior cancer therapy (such as chemotherapy) and has a treatment free interval for more than about any of 3, 6, or 9 months prior to the initiation of the methods described herein. In some embodiments, the individual has received a prior cancer therapy (such as chemotherapy) and has a treatment free interval for more than about any of 12, 18, 24, 36, or 48 months prior to the initiation of the methods described herein. In some embodiments, the individual does not show a symptom of hypersensitivity (such as neuropathy) prior to the initiation of the methods described herein (such as within 12, 9, 6, 5, 4, 3, 2, or 1 month prior to the initiation of the methods described herein). In some embodiments, the individual does not show a symptom of hypersensitivity throughout the treatment period with methods described herein. In some embodiments, the individual does not show a symptom of hypersensitivity upon completion of the treatment with methods described herein.

In some embodiments when the method is directed to treatment of a recurrent ovarian, peritoneal, or fallopian tube cancer, the individual may be confirmed of having an ovarian, peritoneal, or fallopian tube cancer histologically or cytologically. In some embodiments, the individual is determined to have an ovarian, peritoneal, or fallopian tube cancer based on RECIST (Response Evaluation Criteria in Solid Tumors). In some embodiments, the individual has an elevated blood level of Cancer Antigen 125 (CA-125, for example a CA-125 level of more than about 40, 50, 60, 70, 80, or 90 units/ml, or about 2×, 3×, 4×, or more of that of the upper limit of a normal CA-125 level). In some embodiments, the individual has an altered level of a marker that is indicative of an ovarian, peritoneal, or fallopian tube cancer.

In some embodiments, the individual satisfies at least two of the criteria described above. For example, in some embodiments, the individual has a measurable disease by RECIST and an elevated blood level of CA-125. In some embodiments, the individual is confirmed of having an ovarian cancer histologically or cytologically and has only been treated with platinum-based agent(s) prior to administration of the nanoparticle compositions described above. In some embodiments, the individual satisfies at least any of two, three, four, five, or more criteria described above. In some embodiments, the individual satisfies all criteria described above.

In some embodiments, the recurrent cancer (such as recurrent ovarian cancer) is platinum-sensitive. For example, in some embodiments, the individual has received prior platinum-based chemotherapy and has a treatment-free interval for more than about any of 3, 6, or 9 months since the completion of the platinum-based chemotherapy. In some embodiments, the individual has received prior platinum-based chemotherapy and has a treatment-free interval for more than about any of 12, 18, 24, 36, or 48 months since the completion of the platinum-based chemotherapy. Platinum-based chemotherapy includes, but is not limited to, treatment with carboplatin, cisplatin, and oxaliplatin. In some embodiments, the platinum-based chemotherapy is treatment with carboplatin.

The methods described herein comprise administering to the individual an effective amount of a composition comprising nanoparticles comprising a taxane (such as paclitaxel) and a carrier protein (such as albumin). In some embodiments, the taxane nanoparticle composition is administered in conjunction with another chemotherapeutic agent (such as a platinum-based agent). For example, the taxane nanoparticle composition and the other chemotherapeutic agent (such as a platinum-based agent) can be administered sequentially, simultaneously, or concurrently. In some embodiments, the other chemotherapeutic agent (such as platinum-based agent) is administered in the same composition as the nanoparticles comprising taxane and carrier protein. The other chemotherapeutic agent (such as platinum-based agent) can also be formulated into a nanoparticle composition as described herein.

In some embodiments, there is provided a method of treating a recurrent cancer (such as a recurrent gynecological cancer, for example recurrent ovarian, peritoneal, or fallopian tube cancer) in an individual, comprising administering to the individual: a) an effective amount of a composition comprising nanoparticles comprising a taxane (such as paclitaxel) and a carrier protein (such as albumin), and b) an effective amount of a platinum-based agent. In some embodiments, there is provided a method of treating a recurrent cancer (such as a recurrent gynecological cancer, for example recurrent ovarian, peritoneal, or fallopian tube cancer) in an individual, comprising administering to the individual a) an effective amount of a composition comprising nanoparticles comprising paclitaxel and an albumin (such as Abraxane®), and b) an effective amount of a platinum-based agent. Suitable platinum-based agents include, but are not limited to, carboplatin, cisplatin, and oxaliplatin. In some embodiments, the platinum-based agent is carboplatin. In some embodiments, the taxane nanoparticle composition and the platinum-based agent are administered simultaneously. In some embodiments, the taxane nanoparticle composition and the platinum-based agent are administered sequentially. In some embodiments, the taxane nanoparticle composition and the platinum-based agent is administered concurrently.

In some embodiments, there is provided a method of treating a recurrent ovarian cancer in an individual, comprising administering to the individual: a) an effective amount of a composition comprising nanoparticles comprising a taxane (such as paclitaxel) and a carrier protein (such as albumin), and b) an effective amount of a platinum-based agent. In some embodiments, there is provided a method of treating a primary peritoneal cancer in an individual, comprising administering to the individual: a) an effective amount of a composition comprising nanoparticles comprising a taxane (such as paclitaxel) and a carrier protein (such as albumin), and b) an effective amount of a platinum-based agent.

In some embodiments, there is provided a method of treating a recurrent cancer (such as a recurrent gynecological cancer, for example recurrent ovarian, peritoneal, or fallopian tube cancer) in an individual, comprising administering to the individual: a) an effective amount of a composition comprising nanoparticles comprising a taxane (such as paclitaxel) and a carrier protein (such as albumin), and b) an effective amount of a platinum-based agent, wherein the taxane nanoparticle composition and the platinum-based agent are administered concurrently. In some embodiments, there is provided a method of treating a recurrent cancer (such as a recurrent gynecological cancer, for example recurrent ovarian, peritoneal, or fallopian tube cancer) in an individual, comprising administering to the individual: a) an effective amount of a composition comprising nanoparticles comprising a paclitaxel and an albumin (such as Abraxane®), and b)

an effective amount of a platinum-based agent, wherein the paclitaxel nanoparticle composition and the platinum-based agent are administered concurrently.

In some embodiments, there is provided a method of treating a recurrent cancer (such as a recurrent gynecological cancer, for example recurrent ovarian, peritoneal, or fallopian tube cancer) in an individual, comprising administering (for example intravenously or intraperitoneally) to the individual: a) an effective amount of a composition comprising nanoparticles comprising a paclitaxel and an albumin (such as Abraxane®), wherein the amount of the paclitaxel in the composition is at least about 40 mg/m$^2$ (including for example about any of 50 mg/m$^2$, 60 mg/m$^2$, 70 mg/m$^2$, 80 mg/m$^2$, 90 mg/m$^2$, 100 mg/m$^2$, 150 mg/m$^2$, or 200 mg/m$^2$); b) an effective amount of a platinum-based agent (such as the platinum-based agent at the amount of AUC3, AUC4, or AUC6), wherein the taxane nanoparticle composition and the platinum-based agent are administered concurrently. In some embodiments, the method comprises administering a composition comprising nanoparticles comprising paclitaxel and an albumin (such as Abraxane®) at about 100 mg/m$^2$, three out of four weeks, and a platinum-based agent (such as carboplatin) AUC6 every four weeks in the same treatment cycle. In some embodiments, the method comprises administering a composition comprising nanoparticles comprising paclitaxel and an albumin (such as Abraxane®) at about 100 mg/m$^2$, three out of four weeks, and a platinum-based agent (such as carboplatin) AUC5 every four weeks in the same treatment cycle. In some embodiments, the method comprises intravenously administering a composition comprising nanoparticles comprising paclitaxel and an albumin (such as Abraxane®) at about 100 mg/m$^2$, three out of four weeks, and intravenously administering a platinum-based agent (such as carboplatin) AUC5 every four weeks in the same treatment cycle. In some embodiments, the individual is treated with at least any of about one, two, three, four, five, six, seven, eight, or more such treatment cycles.

In some embodiments, there is provided a method of treating recurrent ovarian cancer, comprising intravenously administering a composition comprising nanoparticles comprising paclitaxel and an albumin (such as Abraxane®) at about 100 mg/m$^2$, three out of four weeks, and intravenously administering a platinum-based agent (such as carboplatin) AUC5 (or AUC6) every four weeks in the same treatment cycle. In some embodiments, there is provided a method of treating primary peritoneal cancer, comprising intravenously administering a composition comprising nanoparticles comprising paclitaxel and an albumin (such as Abraxane®) at about 100 mg/m$^2$, three out of four weeks, and intravenously administering a platinum-based agent (such as carboplatin) AUC5 (or AUC6) every four weeks in the same treatment cycle. In some embodiments, the individual is treated with at least any of about one, two, three, four, five, six, seven, eight, or more such treatment cycles.

In some embodiments, the taxane nanoparticle composition is not administered in conjunction with a platinum-based agent, that is, the taxane nanoparticle composition is either administered in a monotherapy dosing regime or administered in conjunction with a chemotherapeutic agent other than a platinum-based agent. In some embodiments, a platinum-based agent is not administered to the individual during the time period in which the individual is receiving one or more doses of the taxane nanoparticle composition. In some embodiments, the individual is not treated with a platinum-based agent concurrently with the administration of the taxane nanoparticle composition.

In some embodiments, the taxane nanoparticle composition can be administered alone, that is, the taxane nanoparticle is administered in a monotherapy dosing regime. For example, in some embodiments, the amount of the taxane nanoparticle composition administered alone is sufficient to result in a complete response in the individual. In some embodiments, the amount of the taxane nanoparticle composition administered alone is sufficient to result in a partial response in the individual. In some embodiments, the amount of the taxane nanoparticle composition administered alone is sufficient to produce an overall response rate of more than about any of 40%, 50%, 60%, or 64% among a population of individuals treated with the taxane nanoparticle composition. In some embodiments, the amount of taxane nanoparticle composition administered alone is sufficient to produce clinical benefit of more than about any of 50%, 60%, 70%, or 77% among a population of individuals treated with the taxane nanoparticle composition.

The taxane nanoparticle compositions described herein comprise nanoparticles comprising taxane (such as paclitaxel) and a carrier protein. In some embodiments, the taxane is paclitaxel, docetaxel, ortataxel, or IDN5390. In some embodiments, the carrier protein is albumin, such as human serum albumin. In some embodiments, the weight ratio of the carrier protein to the taxane in the taxane nanoparticle composition is less than about 18:1 (including for example less than about any of 15:1, 12:1, 10:1, such as 9:1).

In some embodiments, the nanoparticles comprise the taxane coated with a coating comprising the carrier protein (such as albumin). In some embodiments, the coating consists essentially of or consists of the carrier protein. In some embodiments, at least a portion of the carrier protein in the nanoparticle portion of the taxane nanoparticle composition is crosslinked (for example crosslinked by disulfide bonds). In some embodiments, the nanoparticles of the composition comprise at least 5% (including for example at least any of 10%, 15%, 20%, or 25%) of carrier protein that is crosslinked.

In some embodiments, the average or mean diameter of the nanoparticles in the composition is no greater than about 200 nm. In some embodiments, the average or mean diameter of the particles is between about 20 nm to about 400 nm (such as about 40 nm to about 200 nm). In some embodiments, the nanoparticles are sterile-filterable. In some embodiments, the taxane in the nanoparticles is amorphous. In some embodiments, the nanoparticles are substantially free of polymeric core materials. In some embodiments, the nanoparticles comprise a core of taxane that is substantially free of polymeric materials (such as polymertic matrix). In some embodiments, the nanoparticles in the composition have a solid core. In some embodiments, the nanoparticles in the composition have a core that is not aqueous (i.e., other than aqueous core). In some embodiments, the nanoparticles of the composition are substantially free of lipids. In some embodiments, the nanoparticles of the composition are free of lipids.

In some embodiments, the composition comprises more than about 50% (for example more than about any of 60%, 70%, 80%, 90%, or 95%) of the taxane in nanoparticle form. In some embodiments, the weight percentage of the taxane in the nanoparticle portion of the taxane nanoparticle composition is at least about any of 50%, 60%, 70%, 80%, 90%, or 95% of the total weight of the nanoparticle portion of the composition.

In some embodiments, the composition is administered at least about any of once every three weeks, once every two weeks, once a week, twice a week, three times a week, four times a week, five times a week, six times a week, or daily.

Other exemplary dosing frequencies include, but are not limited to, weekly, two out of three weeks; weekly, three out of four weeks; and weekly, four out of five weeks. In some embodiments, the composition is administered (with or without breaks in administration cycles) for at least about any of 1, 2, 3, 4, 5, 6, 7, 8, 9, 10, 11, 12, or more month(s).

In some embodiments, the composition is administered via any of intravenous, intraperitoneal, oral or inhalational routes. In some embodiments, the nanoparticle composition is administered with premedication. In some embodiments, the nanoparticle composition is administered without premedication.

The dose of the taxane in the nanoparticle composition will depend on the type of cancer to be treated, the severity and course of the cancer, the individual's clinical history, and the discretion of the attending physician. Suitable dosages of the taxane in the taxane nanoparticle compositions include, but are not limited to, about any of 50 mg/m$^2$, 60 mg/m$^2$, 75 mg/m$^2$, 80 mg/m$^2$, 90 mg/m$^2$, 100 mg/m$^2$, 120 mg/m$^2$, 125 mg/m$^2$, 150 mg/m$^2$, 160 mg/m$^2$, 180 mg/m$^2$, 200 mg/m$^2$, 210 mg/m$^2$, 220 mg/m$^2$, 230 mg/m$^2$, 240 mg/m$^2$, 260 mg/m$^2$, and 300 mg/m$^2$. Exemplary dosing schedules for the administration of the taxane nanoparticle composition (such as paclitaxel/albumin nanoparticle composition, for example Abraxane®) include, but are not limited to, 260 mg/m$^2$, every three weeks; 60-150 mg/m$^2$, weekly, without break, and 60-150 mg/m$^2$, weekly, three out of four weeks. In addition, the taxane can be administered by following a metronomic dosing regime described herein. In some embodiments, the method comprises administering Abraxane® at 260 mg/m$^2$ by 30 minutes IV infusion every three weeks.

Also provided herein are compositions, kits and unit dosage forms that are suitable for methods described herein. For example, in some embodiments, there is provided a composition for use in the treatment of a recurrent cancer (such as recurrent gynecological cancer for example recurrent ovarian, peritoneal, and fallopian tube cancer), wherein the composition comprises nanoparticles comprising a taxane (such as paclitaxel) and a carrier protein (such as albumin). In some embodiments, there is provided a composition for use in decreasing one or more symptoms resulting from a recurrent cancer (such as recurrent gynecological cancer for example recurrent ovarian, peritoneal, and fallopian tube cancer), wherein the composition comprises nanoparticles comprising a taxane (such as paclitaxel) and a carrier protein (such as albumin). In some embodiments, there is provided a composition for use in the treatment of a recurrent cancer (such as recurrent gynecological cancer for example recurrent ovarian, peritoneal, and fallopian tube cancer) in conjunction with a platinum-based agent, wherein the composition comprises nanoparticles comprising a taxane (such as paclitaxel), wherein the composition comprises nanoparticles comprising a taxane (such as paclitaxel) and a carrier protein (such as albumin). In some embodiments, there is provided a composition for use in decreasing one or more symptoms resulting from a recurrent cancer (such as recurrent gynecological cancer for example recurrent ovarian, peritoneal, and fallopian tube cancer) in conjunction with a platinum-based agent, wherein the composition comprises nanoparticles comprising a taxane (such as paclitaxel) and a carrier protein (such as albumin).

These and other aspects and advantages of the present invention will become apparent from the subsequent detailed description and the appended claims. It is to be understood that one, some, or all of the properties of the various embodiments described herein may be combined to form other embodiments of the present invention.

DETAILED DESCRIPTION OF THE INVENTION

Figure 1A:
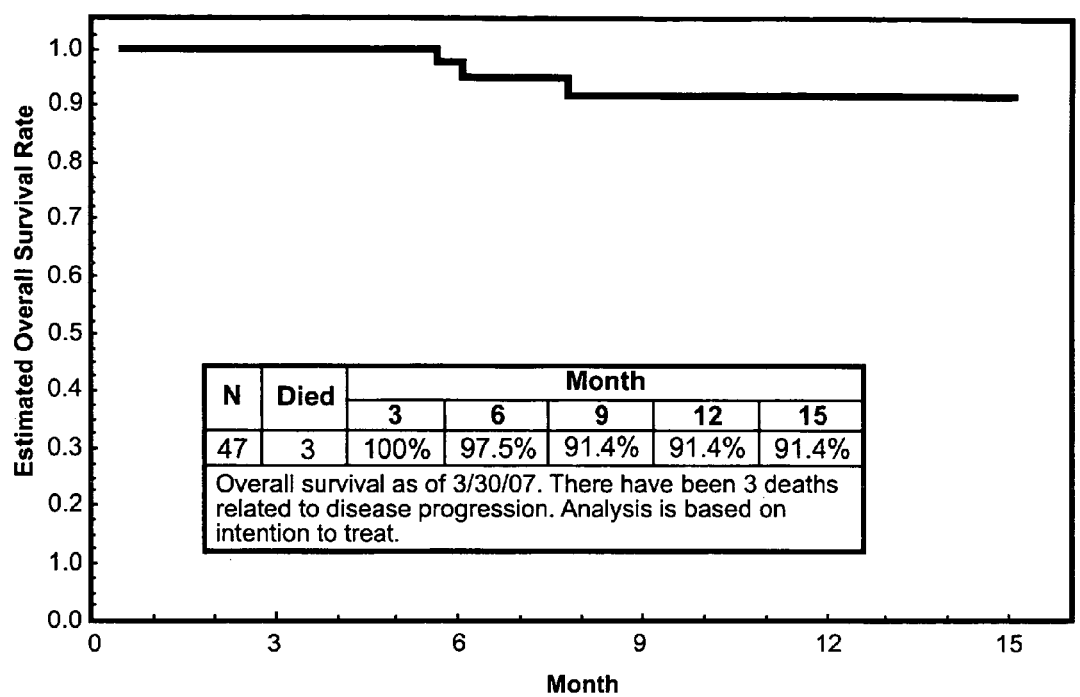
FIG. 1a shows overall survival among patients plotted in terms of months (x-axis) to proportion of survival (y-axis).

The present invention provides methods for the treatment of a recurrent cancer (such as recurrent gynecological cancer) comprising administering to the individual an effective amount of a composition comprising nanoparticles comprising a taxane (such as paclitaxel) and a carrier protein (such as albumin). Specifically, we have shown that a composition comprising nanoparticles comprising a taxane and a carrier protein (hereinafter designated as a "taxane nanoparticle composition"), particularly, a composition comprising nanoparticles comprising paclitaxel and albumin, more particularly, a composition comprising nanoparticles albumin bound paclitaxel ("Nab-paclitaxel"), was very active as a single agent or in combination with a platinum-based agent (carboplatin) in patients with platinum sensitive recurrent gynecological cancer, including recurrent ovarian, peritoneal, or fallopian tube cancer. The overall response rate for the treatment was 64% and the clinical benefit rate was 77%. Complete response was attained in about 70% patients treated with Abraxane® and carboplatin. This demonstrates that a taxane nanoparticle composition is particularly suitable (either as a single agent or in combination with a platinum-based agent) for treating platinum-sensitive recurrent cancer, particularly recurrent gynecological cancer.

Accordingly, the present invention in one aspect provides a method of treating a platinum-sensitive recurrent cancer comprising administering to the individual an effective amount of a composition (such as Nab-paclitaxel or Abraxane®) comprising nanoparticles comprising a taxane (such as paclitaxel) and a carrier protein (such as albumin). In another aspect, there is provided a method of treating a recurrent ovarian cancer (such as platinum-sensitive recurrent ovarian cancer) comprising administering to the individual an effective amount of a composition (such as Nab-paclitaxel or Abraxane®) comprising nanoparticles comprising a taxane (such as paclitaxel) and a carrier protein (such as albumin).

DEFINITIONS

As used herein, "the composition" or "compositions" includes and is applicable to compositions of the invention. The invention also provides pharmaceutical compositions comprising the components described herein.

Reference to "taxane" herein applies to a taxane or its derivatives and accordingly the invention contemplates and includes all these variations. Reference to "taxane" is to simplify the description and is exemplary. Taxanes include, but are not limited to, compounds that are structurally similar to or are in the same general chemical class such as paclitaxel (i.e., taxol), docetaxel (i.e., taxotere), or ortataxel, and pharmaceutically acceptable salts, derivatives, or analogs of paclitaxel, docetaxel, and ortataxel. Taxanes are antimicrobial agents that inhibit cell replication by promoting the assembly and stabilization of microtubule from tubulin dimers.

Unless clearly indicated otherwise, "an individual" as used herein refers to human.

As used herein, "treatment" or "treating" is an approach for obtaining beneficial or desired results including clinical results. For purposes of this invention, beneficial or desired clinical results include, but are not limited to, one or more of the following: decreasing one or more symptoms resulting from the disease, diminishing the extent of the disease, stabilizing the disease (e.g., preventing or delaying the worsening of the disease), delay or slowing the progression of the disease, ameliorating the disease state, decreasing the dose of one or more other medications required to treat the disease, increasing the quality of life, and/or prolonging survival (including overall survival and progression free survival. In some embodiments, the composition reduces the severity of one or more symptoms associated with cancer by at least about any of 10%, 20%, 30%, 40%, 50%, 60%, 70%, 80%, 90%, 95%, or 100% compared to the corresponding symptom in the same subject prior to treatment or compared to the corresponding symptom in other subjects not receiving the composition. Also encompassed by "treatment" is a reduction of pathological consequence of cancer. The methods of the invention contemplate any one or more of these aspects of treatment.

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of subjects. Cancer development can be detectable using standard methods, such as routine physical exams or x-ray. Development may also refer to disease progression that may be initially undetectable and includes occurrence and onset.

"Adjuvant setting" refers to a clinical setting in which an individual has had a history of ovarian cancer, and generally (but not necessarily) been responsive to therapy, which includes, but is not limited to, surgery (e.g., surgical resection), radiotherapy, and chemotherapy. However, because of their history of the cancer, these individuals are considered at risk of development of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated.

"Neoadjuvant setting" refers to a clinical setting in which the method is be carried out before the primary/definitive therapy.

As used herein, an "at risk" individual is an individual who is at risk of developing cancer. An individual "at risk" may or may not have detectable disease, and may or may not have displayed detectable disease prior to the treatment methods described herein. "At risk" denotes that an individual has one or more so-called risk factors, which are measurable parameters that correlate with development of cancer, which are described herein. An individual having one or more of these risk factors has a higher probability of developing cancer than an individual without these risk factor(s).

As used herein, by "pharmaceutically active compound" is meant a chemical compound that induces a desired effect, e.g., treating, stabilizing, preventing, and/or delaying cancer.

As used herein, by "combination therapy" is meant a first therapy that includes nanoparticles comprising nanoparticles comprising a taxane (e.g. paclitaxel) and a carrier protein in conjunction with a second therapy (e.g., surgery or a therapeutic agent) useful for treating, stabilizing, preventing, and/or delaying cancer. Administration in "conjunction with" another compound includes administration in the same or different composition(s), either sequentially, simultaneously, or continuously. In some embodiments, the combination therapy optionally includes one or more pharmaceutically acceptable carriers or excipients, non-pharmaceutically active compounds, and/or inert substances.

The term "effective amount" refers to an amount of a drug effective to treat cancer in the patient. The effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response or a complete response), increase overall survival time, and/or improve one or more symptoms of cancer (e.g. as assessed by FOSI).

As is understood in the art, an "effective amount" may be in one or more doses, i.e., a single dose or multiple doses may be required to achieve the desired treatment endpoint. An effective amount may be considered in the context of administering one or more therapeutic agents, and a nanoparticle composition (e.g., a composition including a taxane (e.g., paclitaxel) and a carrier protein) may be considered to be given in an effective amount if, in conjunction with one or more other agents, a desirable or beneficial result may be or is achieved.

In some embodiments, the amount of the composition is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

The term "proteins" refers to polypeptides or polymers of amino acids of any length (including full length or fragments), which may be linear or branched, comprise modified amino acids, and/or be interrupted by non-amino acids. The term also encompasses an amino acid polymer that has been modified naturally or by intervention, including, for example, disulfide bond formation, glycosylation, lipidation, acetylation, phosphorylation, or any other manipulation or modification. Also included within this term are, for example, polypeptides containing one or more analogs of an amino acid (including, for example, unnatural amino acids, etc.), as well as other modifications known in the art. The proteins described herein may be naturally-occurring, i.e., obtained or derived from a natural source (e.g., blood) or synthesized (e.g., chemically synthesized or by synthesized by recombinant DNA techniques). Exemplary carrier proteins are described herein.

The term "antimicrobial agent" used herein refers to an agent that is capable of inhibiting (e.g., delaying, reducing, slowing, and/or preventing) the growth of one or more microorganisms. Significant microbial growth can be measured or indicated by a number of ways known in the art, such as one or more of the following: (i) microbial growth in a composition that is enough to cause one or more adverse effects to an individual when the composition is administered to the individual; (ii) more than about 10-fold increase in microbial growth over a certain period of time (for example over a 24 hour period) upon extrinsic contamination (e.g., exposure to $10-10^3$ colony forming units at a temperature in the range of 20 to 25° C.). Other indicia of significant microbial growth are described in U.S. Patent Application Publication No. US20070117744 (U.S. Ser. No. 11/514,030, filed Aug. 30, 2006), which is hereby incorporated by reference in its entirety.

"Sugar" as used herein includes, but is not limited to, monosaccharides, disaccharides, polysaccharides, and derivatives or modifications thereof. Suitable sugars for compositions described herein include, for example, mannitol, sucrose, fructose, lactose, maltose, and trehalose.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Survival" refers to the patient remaining alive, and includes overall survival as well as progression free survival.

"Overall survival" refers to the patient remaining alive for a defined period of time, such as 1 year, 5 years, etc. from the time of diagnosis or treatment.

"Progression free survival" refers to the patient remaining alive, without the cancer progressing or getting worse.

By "prolonging survival" is meant increasing overall or progression free survival in a treated patient relative to an untreated patient (e.g. relative to a patient not treated with a taxane nanoparticle composition).

As used herein, reference to "not" a value or parameter generally means and describes "other than" a value or parameter. For example, if a taxane is not administered, it means an agent other than a taxane is administered.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

Methods of the Present Invention

The present invention provides methods for the treatment of a recurrent cancer (such as a recurrent gynecological cancer for example recurrent ovarian, peritoneal, or fallopian tube cancer) by administering a composition comprising nanoparticles comprising a taxane and a carrier protein. In some embodiments, there is provided a method of treating a recurrent cancer in an individual, comprising administering to the individual an effective amount of a composition comprising nanoparticles comprising a taxane and a carrier protein. In some embodiments, the recurrent cancer is platinum sensitive. In some embodiments, the recurrent cancer is platinum resistant. In some embodiments, the recurrent cancer is any of recurrent ovarian cancer, recurrent peritoneal cancer, recurrent fallopian tube cancer, recurrent malignant mixed mullerian tumor, and serous endo.

In some embodiments, there is provided a method of treating a recurrent ovarian, peritoneal, or fallopian tube cancer in an individual, comprising administering to the individual an effective amount of a composition comprising nanoparticles comprising a taxane and a carrier protein. In some embodiments, there is provided a method of treating a platinum-sensitive recurrent ovarian, peritoneal, or fallopian tube cancer in an individual, comprising administering to the individual an effective amount of a composition comprising nanoparticles comprising a taxane and a carrier protein. In some embodiments, the recurrent cancer is a recurrent ovarian cancer (such as a recurrent epithelial ovarian cancer). In some embodiments, the recurrent cancer is a recurrent peritoneal cancer. In some embodiments, the recurrent cancer is a recurrent fallopian tube cancer (including for example papillary serous adenocarcinomas, sarcomas, and transitional cell carcinomas).

In some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the individual has received a prior chemotherapy and has a treatment free interval for more about any of 3, 6, 9 months since the completion of prior chemotherapy. In some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the individual has received a prior chemotherapy and has a treatment free interval for more about any of 12, 18, 24, 36, or 48 months since the completion of prior chemotherapy. In some embodiments, the prior chemotherapy has a different mechanism of action than that of the taxane-based therapy. In some embodiments, the individual has only been treated with platinum-based agent(s) prior to the administration of the taxane nanoparticle composition. In some embodiments, the individual has only been treated with one dosing regime prior to the administration of the taxane nanoparticle composition. In some embodiments, the individual has not previously been treated with a taxane-based therapy.

In some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the individual has received prior platinum-based chemotherapy and has a treatment free interval for more than about any of 3, 6, 9 months since the completion of the platinum-based chemotherapy. In some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the individual has received prior platinum-based chemotherapy and has a treatment free interval for more than about any of 12, 18, 24, 36, or 38 months since the completion of the platinum-based chemotherapy. In some embodiments, the method further comprises administering to the individual an effective amount of a platinum-based agent (such as carboplatin). In some embodiments, the composition comprising nanoparticles comprising a taxane and a carrier protein is not administered in conjunction with a platinum agent, that is, the composition comprising nanoparticles comprising a taxane and a carrier protein is either administered alone or administered in conjunction with a chemotherapeutic agent other than a platinum-based agent.

In some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the individual has received a prior chemotherapy and has a treatment free interval for more about any of 3, 6, 9 months prior to the initiation of the treatment method with the taxane nanoparticle composition. In some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the individual has received a prior chemotherapy and has a treatment free interval for more about any of 12, 18, 24, 36, or 48 months prior to the initiation of the treatment method with the taxane nanoparticle composition. In some embodiments, the prior chemotherapy has a different mechanism of action than that of the taxane-based therapy. In some embodiments, the individual has only been treated with platinum-based agent(s) prior to the administration of the taxane nanoparticle composition. In some embodiments, the individual has only been treated with one dosing regime prior to the administration of the taxane nanoparticle composition. In some embodiments, the individual has not previously been treated with a taxane-based therapy.

In some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the individual has received prior platinum-based chemotherapy and has a treatment free interval for more than about any of 3, 6, 9 months prior to the initiation of the treatment method with the taxane nanoparticle composition. In some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the individual has received prior platinum-based chemotherapy and has a treatment free interval for more than about any of 12, 18, 24, 36, or 38 months prior to the initiation of the treatment method with the taxane nanoparticle composition. In some embodiments, the method further comprises administering to the individual an effective amount of a platinum-based agent. In some embodiments, the composition comprising nanoparticles comprising a taxane and a carrier protein is not administered in conjunction with a platinum agent, that is, the composition comprising nanoparticles comprising a taxane and a carrier protein is either administered alone or administered in conjunction with a chemotherapeutic agent other than a platinum-based agent.

In some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the individual does not show a symptom of hypersensitivity (such as neuropathy) prior to the initiation of the treatment method with the taxane nanoparticle composition. In some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the individual does not show a symptom of hypersensitivity throughout the treatment period. In some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the individual does not show symptoms of hypersensitivity upon completion of the treatment.

In some embodiments, the composition comprising nanoparticles comprising a taxane and a carrier protein is administered alone. For example, in some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the amount of the composition administered to the individual alone is effective to result in a complete response in the individual. In some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the amount of the composition administered to the individual alone is effective to result in a partial response in the individual.

In some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the amount of the composition administered to the individual alone is sufficient to produce an overall response rate of more than about any of 40%, 50%, 60%, or 64% among a population of individuals treated with the composition. In some embodiments, there is provided a method of treating a recurrent cancer (such as a recurrent gynecological cancer for example recurrent ovarian, peritoneal, or fallopian tube cancer) in an individual, comprising administering to the individual an effective amount of a composition comprising nanoparticles comprising a taxane (such as paclitaxel) and a carrier protein (such as albumin), wherein the amount of the composition administered to the individual alone is sufficient to produce clinical benefit of more than about any of 50%, 60%, 70%, or 77% among a population of individuals treated with the composition.

In some embodiments, the method comprises administering to the individual an effective amount of a composition comprising nanoparticles comprising paclitaxel and albumin. In some embodiments, the method comprises administering to the individual an effective amount of a composition comprising nanoparticles comprising a taxane (such as paclitaxel) and a carrier protein (such as albumin), wherein average or mean diameter of the nanoparticles in the composition is less than about 200 nm. In some embodiments, the method comprises administering to the individual an effective amount of a composition comprising nanoparticles comprising a taxane (such as paclitaxel) and a carrier protein (such as albumin), wherein the nanoparticles comprise taxane coated with a coating comprising the carrier protein. In some embodiments, the method comprises administering to the individual an effective amount of a Nab-paclitaxel (such as Abraxane®). For example, in some embodiments, there is provided a method of treating a platinum-sensitive recurrent ovarian, peritoneal, or fallopian tube cancer in the individual, comprising administering to the individual an effective amount of Nab-paclitaxel or Abraxane®.

In some embodiments, there is provided a method of treating a recurrent ovarian, peritoneal, or fallopian tube cancer (such as a platinum-resistant ovarian, peritoneal, or fallopian tube cancer) in an individual, comprising administering to the individual about 50 mg/m$^2$ to about 300 mg/m$^2$ (including for example about 260 mg/m$^2$) Nab-paclitaxel or Abraxane®. In some embodiments, the Nab-paclitaxel or Abraxane® is administered every three weeks. In some embodiments, the Nab-paclitaxel or Abraxane® is administered intravenously (such as by i.v. infusion over a period of about 30 minutes or less). In some embodiments, the Nab-paclitaxel or Abraxane® is administered intraperitoneally.

The methods of the present invention are useful for any one or more of the following (and thus in various embodiments can achieve and/or include any one or more of the following): 1) decreasing one or more symptoms resulting from recurrent cancer (such as recurrent gynecological cancer for example recurrent ovarian, peritoneal, and fallopian tube cancer); 2) increasing overall response rate of a recurrent cancer (such as recurrent gynecological cancer for example recurrent ovarian, peritoneal, and fallopian tube cancer); 3) increasing partial response rate of a recurrent cancer (such as recurrent gynecological cancer for example recurrent ovarian, peritoneal, and fallopian tube cancer); 4) increasing complete response rate of a recurrent cancer (such as recurrent gynecological cancer for example recurrent ovarian, peritoneal, and fallopian tube cancer); 5) delaying disease progression of an individual with a recurrent cancer (such as recurrent gynecological cancer for example recurrent ovarian, peritoneal, and fallopian tube cancer); 6) increasing the quality of life in an individual with recurrent cancer (such as recurrent gynecological cancer for example recurrent ovarian, peritoneal, and fallopian tube cancer); 7) prolonging overall survival of an individual having recurrent cancer (such as recurrent gynecological cancer for example recurrent ovarian, peritoneal, and fallopian tube cancer); and 8) prolonging progression-free survival of an individual having recurrent cancer (such as recurrent gynecological cancer for example recurrent ovarian, peritoneal, and fallopian tube cancer).

Accordingly, in some embodiments, there is provided a method of decreasing one or more symptoms resulting from a recurrent cancer (such as recurrent gynecological cancer for example recurrent ovarian, peritoneal, and fallopian tube cancer), comprising administering to the individual an effective amount of a composition comprising nanoparticles comprising a taxane (such as paclitaxel) and a carrier protein (such as albumin). In some embodiments, there is provided a method of decreasing one more symptoms resulting from a recurrent cancer (such as recurrent gynecological cancer for example recurrent ovarian, peritoneal, and fallopian tube cancer), comprising administering to the individual an effective amount of Nab-paclitaxel or Abraxane®.

In some embodiments, there is provided a method of increasing response rate of recurrent cancer (such as recurrent gynecological cancer for example recurrent ovarian, peritoneal, and fallopian tube cancer), comprising administering to the individual an effective amount of a composition comprising nanoparticles comprising a taxane (such as paclitaxel) and a carrier protein (such as albumin). In some embodiments, there is provided a method of increasing response rate of recurrent cancer (such as recurrent gynecological cancer for example recurrent ovarian, peritoneal, and fallopian tube cancer), comprising administering to the individual an effective amount of Nab-paclitaxel or Abraxane®.

In some embodiments, there is provided a method of delaying disease progression of an individual with recurrent cancer (such as recurrent gynecological cancer for example recurrent ovarian, peritoneal, and fallopian tube cancer), comprising administering to the individual an effective amount of a composition comprising nanoparticles comprising a taxane (such as paclitaxel) and a carrier protein (such as albumin). In some embodiments, there is provided a method of delaying disease progression of an individual with recurrent cancer (such as recurrent gynecological cancer for example recurrent ovarian, peritoneal, and fallopian tube cancer), comprising administering to the individual an effective amount of Nab-paclitaxel or Abraxane®.

In some embodiments, there is provided a method of prolonging survival of an individual having recurrent cancer (such as recurrent gynecological cancer for example recurrent ovarian, peritoneal, and fallopian tube cancer), comprising administering to the individual an effective amount of a composition comprising nanoparticles comprising a taxane (such as paclitaxel) and a carrier protein (such as albumin). In some embodiments, there is provided a method of prolonging survival of an individual having recurrent cancer (such as recurrent gynecological cancer for example ovarian, peritoneal, and fallopian tube cancer), comprising administering to the individual an effective amount of Nab-paclitaxel or Abraxane®.

In some embodiments, there is provided a method of treating a recurrent ovarian, peritoneal, or fallopian tube cancer in an individual, comprising administering to the individual an effective amount of a composition comprising nanoparticles comprising a taxane and a carrier protein, wherein one or more symptoms resulting from the recurrent cancer is decreased. In some embodiments, there is provided a method of treating a recurrent ovarian, peritoneal, or fallopian tube cancer in an individual, comprising administering to the individual an effective amount of a composition comprising nanoparticles comprising a taxane and a carrier protein, wherein the individual has a partial response to treatment upon completion of less than about any of one, two, three, four, five, six, seven, or eight treatment cycles. In some embodiments, there is provided a method of treating a recurrent ovarian, peritoneal, or fallopian tube cancer in an individual, comprising administering to the individual an effective amount of a composition comprising nanoparticles comprising a taxane and a carrier protein, wherein the individual has a complete response to treatment upon completion of less than about any of one, two, three, four, five, six, seven, or eight treatment cycles. In some embodiments, the treatment cycle is four weeks. In some embodiments, the treatment cycle is three weeks.

In some embodiments, there is provided a method of treating a recurrent ovarian, peritoneal, or fallopian tube cancer in an individual, comprising administering to the individual an effective amount of a composition comprising nanoparticles comprising a taxane and a carrier protein, wherein the individual is disease free for at least about any of 0.5, 1, 2, 3, 4, 5, 6, 7, 8, 9, 10, 12, 14, 16, 18, 20, 22, or 24 months upon completion of the treatment. In some embodiments, there is provided a method of treating a recurrent ovarian, peritoneal, or fallopian tube cancer in an individual, comprising administering to the individual an effective amount of a composition comprising nanoparticles comprising a taxane and a carrier protein, wherein the individual does not show a symptom resulting from the recurrent cancer for at least about any of 0.5, 1, 2, 3, 4, 5, 6, 7, 8, 9, 10, 12, 14, 16, 18, 20, 22, or 24 months upon completion of the treatment. In some embodiments, there is provided a method of treating a recurrent ovarian, peritoneal, or fallopian tube cancer in an individual, comprising administering to the individual an effective amount of a composition comprising nanoparticles comprising a taxane and a carrier protein, wherein the individual has a reduced CA-125 level (such as a level below about any of 70%, 60%, 50%, 40%, 30%, 20%, 10% of the level prior to the treatment) upon completion of the treatment. In some embodiments, the individual has a reduced CA-125 level for at least about any of 0.5, 1, 2, 3, 4, 5, 6, 7, 8, 9, 10, 12, 14, 16, 18, 20, 22, or 24 months upon completion of the treatment.

In some embodiments, there is provided a method of treating a recurrent ovarian, peritoneal, or fallopian tube cancer in an individual, comprising administering (for example intravenously or intraperitoneally) to the individual an effective amount of a composition comprising nanoparticles comprising a taxane (such as paclitaxel) and a carrier protein (such as albumin), wherein the amount of the taxane per administration is at least about 50 mg/m$^2$ (such as at least about any of 70 mg/m$^2$, 100 mg/m$^2$, 150 mg/m$^2$, 200 mg/m$^2$, or 260 mg/m$^2$), and wherein one or more symptoms resulting from the recurrent cancer is decreased. In some embodiments, there is provided a method of treating a recurrent ovarian, peritoneal, or fallopian tube cancer in an individual, comprising administering (for example intravenously or intraperitoneally) to the individual an effective amount of Abraxane®, wherein the amount of paclitaxel per administration is at least about 50 mg/m$^2$ (such as at least about any of 70 mg/m$^2$, 100 mg/m$^2$, 150 mg/m$^2$, 200 mg/m$^2$, or 260 mg/m$^2$), and wherein one or more symptoms resulting from the recurrent cancer is decreased. In some embodiments, the composition is administered once every three weeks. In some embodiments, the composition is administered weekly. In some embodiments, the composition is administered three out of four weeks. In some embodiments, the individual does not show a symptom of hypersensitivity (such as neuropathy) prior to the initiation of the treatment. In some embodiments, the individual does not show a symptom of hypersensitivity throughout the treatment period. In some embodiments, the individual does not show a symptom of hypersensitivity upon completion of the treatment.

In some embodiments, the taxane nanoparticle composition is administered in conjunction with another chemotherapeutic agent (such as a platinum-based agent). For example, in some embodiments, the taxane nanoparticle composition and the other chemotherapeutic agent (such as a platinum-based agent) are administered simultaneously. The term "simultaneous administration," as used herein, means that the taxane nanoparticle composition and the other chemotherapeutic agent are administered with a time separation of no more than about 15 minute(s), such as no more than about any of 10, 5, or 1 minutes. When the drugs are administered simultaneously, the taxane in the nanoparticles and the other chemotherapeutic agent may be contained in the same composition (e.g., a composition comprising both the nanoparticles and the other chemotherapeutic agent) or in separate compositions (e.g., the nanoparticles are contained in one composition and the other chemotherapeutic agent is contained in another composition). For example, the taxane and the other chemotherapeutic agent may be present in a single composition containing at least two different nanoparticles, wherein some of the nanoparticles in the composition comprise the taxane and a carrier protein, and some of the other nanoparticles in the composition comprise the other chemotherapeutic agent and a carrier protein. In some embodiments, only the taxane is contained in nanoparticles. In some embodiments, simultaneous administration of the drug in the nanoparticle composition and the other chemotherapeutic agent can be combined with supplemental doses of the taxane and/or the other chemotherapeutic agent.

In some embodiments, the nanoparticle composition and the other chemotherapeutic agent (such as the platinum-based agent) are administered sequentially. The term "sequential administration" as used herein means that the taxane in the nanoparticle composition and the other chemotherapeutic agent are administered with a time separation of more than about 15 minutes, such as more than about any of 20, 30, 40, 50, 60 or more minutes. Either the nanoparticle composition or the other chemotherapeutic agent may be administered first. The nanoparticle composition and the other chemotherapeutic agent are contained in separate compositions, which may be contained in the same or different packages.

In some embodiments, the administration of the nanoparticle composition and the other chemotherapeutic agent are concurrent, i.e., the administration period of the nanoparticle composition and that of the other chemotherapeutic agent overlap with each other. In some embodiments, the nanoparticle composition and the other chemotherapeutic agent are administered in the same treatment cycle(s).

The dosing frequency of the drug-containing nanoparticle composition and the other chemotherapeutic agent may be adjusted over the course of the treatment, based on the judgment of the administering physician. When administered separately, the drug-containing nanoparticle composition and the other chemotherapeutic agent can be administered at different dosing frequency or intervals. For example, the drug-containing nanoparticle composition can be administered weekly, while a chemotherapeutic agent can be administered more or less frequently. In some embodiments, sustained continuous release formulation of the drug-containing nanoparticle and/or chemotherapeutic agent may be used. Various formulations and devices for achieving sustained release are known in the art.

In some embodiments, there is provided a method of treating a recurrent cancer (such as a recurrent gynecological cancer, for example recurrent ovarian, peritoneal, or fallopian tube cancer) in an individual, comprising administering to the individual: a) an effective amount of a composition comprising nanoparticles comprising a taxane (such as paclitaxel) and a carrier protein (such as albumin), and b) an effective amount of a platinum-based agent. In some embodiments, there is provided a method of treating a recurrent cancer (such as a recurrent gynecological cancer, for example recurrent ovarian, peritoneal, or fallopian tube cancer) in an individual, comprising administering to the individual a) an effective amount of a composition comprising nanoparticles comprising paclitaxel and an albumin (such as Abraxane®), and b) an effective amount of a platinum-based agent. Suitable platinum-based agents include, but are not limited to, carboplatin, cisplatin, and oxaliplatin. In some embodiments, the platinum-based agent is carboplatin. In some embodiments, the taxane nanoparticle composition and the platinum-based agent are administered simultaneously. In some embodiments, the taxane nanoparticle composition and the platinum-based agent are administered sequentially. In some embodiments, the taxane nanoparticle composition and the platinum-based agent is administered concurrently.

In some embodiments, there is provided a method of treating a recurrent ovarian cancer in an individual, comprising administering to the individual: a) an effective amount of a composition comprising nanoparticles comprising a taxane (such as paclitaxel) and a carrier protein (such as albumin), and b) an effective amount of a platinum-based agent. In some embodiments, there is provided a method of treating a primary peritoneal cancer in an individual, comprising administering to the individual: a) an effective amount of a composition comprising nanoparticles comprising a taxane (such as paclitaxel) and a carrier protein (such as albumin), and b) an effective amount of a platinum-based agent.

In some embodiments, there is provided a method of treating a recurrent cancer (such as a recurrent gynecological cancer, for example recurrent ovarian, peritoneal, or fallopian tube cancer) in an individual, comprising administering to the individual: a) an effective amount of a composition comprising nanoparticles comprising a taxane (such as paclitaxel) and a carrier protein (such as albumin), and b) an effective amount of a platinum-based agent, wherein the taxane nanoparticle composition and the platinum-based agent are administered concurrently. In some embodiments, there is provided a method of treating a recurrent cancer (such as a recurrent gynecological cancer, for example recurrent ovarian, peritoneal, or fallopian tube cancer) in an individual, comprising administering to the individual: a) an effective amount of a composition comprising a paclitaxel and an albumin (such as Abraxane®), and b) an effective amount of a platinum-based agent, wherein the paclitaxel nanoparticle composition and the platinum-based agent are administered concurrently.

In some embodiments, there is provided a method of treating a recurrent cancer (such as a recurrent gynecological cancer, for example recurrent ovarian, peritoneal, or fallopian tube cancer) in an individual, comprising administering (for example intravenously or intraperitoneally) to the individual: a) an effective amount of a composition comprising nanoparticles comprising a paclitaxel and an albumin (such as Abraxane®), wherein the amount of the paclitaxel in the composition is at least about 40 mg/m$^2$ (including for example about any of 50 mg/m$^2$, 60 mg/m$^2$, 70 mg/m$^2$, 80 mg/m$^2$, 90 mg/m$^2$, 100 mg/m$^2$, 150 mg/m$^2$, or 200 mg/m$^2$); b) an effective amount of a platinum-based agent (such as the platinum-based agent at the amount of AUC3, AUC4, or AUC6), wherein the taxane nanoparticle composition and the platinum-based agent are administered concurrently. In some embodiments, the method comprises administering a composition comprising nanoparticles comprising paclitaxel and an albumin (such as Abraxane®) at about 100 mg/m$^2$, three out of four weeks, and a platinum-based agent (such as carboplatin) AUC6 every four weeks in the same treatment cycle. In some embodiments, the method comprises administering a composition comprising nanoparticles comprising paclitaxel and an albumin (such as Abraxane®) at about 100 mg/m$^2$, three out of four weeks, and a platinum-based agent (such as carboplatin) AUC5 every four weeks in the same treatment cycle. In some embodiments, the method comprises intravenously administering a composition comprising nanoparticles comprising paclitaxel and an albumin (such as Abraxane®) at about 100 mg/m$^2$, three out of four weeks, and intravenously administering a platinum-based agent (such as carboplatin) AUC5 every four weeks in the same treatment cycle. In some embodiments, the individual is treated with at least any of about one, two, three, four, five, six, seven, eight, or more such treatment cycles.

In some embodiments, there is provided a method of treating recurrent ovarian cancer, comprising intravenously administering a composition comprising nanoparticles comprising paclitaxel and an albumin (such as Abraxane®) at about 100 mg/m$^2$, three out of four weeks, and intravenously administering a platinum-based agent (such as carboplatin) AUC5 (or AUC6) every four weeks in the same treatment cycle. In some embodiments, there is provided a method of treating primary peritoneal cancer, comprising intravenously administering a composition comprising nanoparticles comprising paclitaxel and an albumin (such as Abraxane®) at about 100 mg/m$^2$, three out of four weeks, and intravenously administering a platinum-based agent (such as carboplatin) AUC5 (or AUC6) every four weeks in the same treatment cycle. In some embodiments, the individual is treated with at least any of about one, two, three, four, five, six, seven, eight, or more such treatment cycles.

Individual Having Recurrent Cancer

The present invention provides a method of treating a recurrent cancer (such as recurrent gynecological cancer for example recurrent ovarian, peritoneal, and fallopian tube cancer) in an individual. A "recurrent" cancer is one which has regrown, either at the initial site or at a distant site, after a response to initial therapy. In some embodiments, the length of time between the completion of initial therapy and the development of recurrent disease is longer than about 3 month, including for example longer than about any of 4, 5, 6, 7, 8, 9, 10, or 11 months. In some embodiments, the length of time between the completion of initial therapy and the development of recurrent disease is longer than about 12 month, including for example, longer than about any of 14, 16, 18, 20, 22, 24, 36, or 48 months.

In some embodiments, the recurrent cancer is a recurrent gynecological cancer. "Gynecologic cancer" used herein refers to a cancer originating in the female reproductive organs. It includes cancers of the cervix, fallopian tubes, ovaries, uterus, vagina and vulva. In some embodiments, the recurrent cancer is a recurrent ovarian cancer. In some embodiments, the cancer is ovarian epithelial cancer. Exemplary ovarian epithelial cancer histological classifications include: serous cystomas (e.g., serous benign cystadenomas, serous cystadenomas with proliferating activity of the epithelial cells and nuclear abnormalities but with no infiltrative destructive growth, or serous cystadenocarcinomas), mucinous cystomas (e.g., mucinous benign cystadenomas, mucinous cystadenomas with proliferating activity of the epithelial cells and nuclear abnormalities but with no infiltrative destructive growth, or mucinous cystadenocarcinomas), endometrioid tumors (e.g., endometrioid benign cysts, endometrioid tumors with proliferating activity of the epithelial cells and nuclear abnormalities but with no infiltrative destructive growth, or endometrioid adenocarcinomas), clear cell (mesonephroid) tumors (e.g., begin clear cell tumors, clear cell tumors with proliferating activity of the epithelial cells and nuclear abnormalities but with no infiltrative destructive growth, or clear cell cystadenocarcinomas), unclassified tumors that cannot be allotted to one of the above groups, or other malignant tumors.

In some embodiments, the recurrent cancer is a recurrent ovarian germ cell tumor. Exemplary histologic subtypes include dysgerminomas or other germ cell tumors (e.g., endodermal sinus tumors such as hepatoid or intestinal tumors, embryonal carcinomas, olyembryomas, choriocarcinomas, teratomas, or mixed form tumors). Exemplary teratomas are immature teratomas, mature teratomas, solid teratomas, and cystic teratomas (e.g., dermoid cysts such as mature cystic teratomas, and dermoid cysts with malignant transformation). Some teratomas are monodermal and highly specialized, such as struma ovarii, carcinoid, struma ovarii and carcinoid, or others (e.g., malignant neuroectodermal and ependymomas).

In some embodiments, the recurrent cancer is a recurrent peritoneal cancer. In some embodiments, the recurrent cancer is a recurrent fallopian tube cancer (including for example papillary serous adenocarcinomas, sarcomas, and transitional cell carcinomas). Other recurrent cancers such as recurrent malignant mixed mullerian tumor and serous endo can also be treated.

Recurrence of ovarian, peritoneal, or fallopian tube cancer can be determined, for example, based on bimanual pelvic examinations, serial measurements of CA-125 or other tumor markers, one or more imaging studies reassessments, and second-look laparotomy. Imaging studies such as CT, PET, or a CT/PET combination can also be used. In some embodiments, recurrence of ovarian, peritoneal, or fallopian tube cancer can be determined based on Response Evaluation Criteria in Solid Tumors (RECIST).

"Individual" used herein refers to human. In some embodiments, the individual is a woman who is about 40 to about 85 years old, including for example about 60 to about 70 years old. In some embodiments, the individual has an Eastern Cooperative Oncology Group (ECOG) performance status of 0-2 (such as any of 0, 1, or 2) prior to the administration of the taxane nanoparticle composition. In some embodiments, the individual has received a prior chemotherapy and has a treatment free interval for more than about any of 3, 6, or 9 months since the completion of prior chemotherapy. In some embodiments, the individual has received a prior chemotherapy and has a treatment free interval for more than about any of 12, 18, 24, 36, or 48 months since the completion of prior chemotherapy. In some embodiments, the prior chemotherapy has a different mechanism of action than that of the taxane. In some embodiments, the individual has only been treated with platinum-based agent(s) prior to the administration of the taxane nanoparticle composition. In some embodiments, the individual has only been treated with one dosing regime prior to the administration of the taxane nanoparticle composition. In some embodiments, the individual has not previously been treated with a taxane-based therapy.

In some embodiments, when the method is directed to treatment of a recurrent ovarian, peritoneal, or fallopian tube cancer, the individual is confirmed of having an ovarian, peritoneal, or fallopian tube cancer histologically or cytologically. In some embodiments, the individual is determined to have an ovarian, peritoneal, or fallopian tube cancer based on RECIST. In some embodiments, the individual has an elevated blood level of Cancer Antigen 125 (CA-125, for example a CA-125 level of more than about 40, 50, 60, 70, 80, or 90 units/ml, or about 2×, 3×, 4×, or more of that of the upper limit of a normal CA-125 level). In some embodiments, the individual has an altered expression level of another marker that is indicative of a recurrent ovarian, peritoneal, and fallopian tube cancer.

The individual being treated may have one or more risk factors associated with a higher probability of developing ovarian, peritoneal, and fallopian tube cancer. These risk factors include, but are not limited to, age, sex, race, diet, history of previous disease, presence of precursor disease, genetic (i.e., hereditary) considerations, and environmental exposure. In some embodiments, the individual may be a human who is genetically or otherwise predisposed to developing ovarian, peritoneal, and fallopian tube cancer, particularly recurrent ovarian, peritoneal, and fallopian tube cancer.

Individuals at risk for ovarian, peritoneal, and fallopian tube cancer include, for example, those having relatives who have experienced this disease, and those whose risk is determined by analysis of genetic or biochemical markers. For example, the individual may be a human who has a gene, genetic mutation, or polymorphism associated with ovarian cancer (e.g., BRCA1 or BRCA2) or has one or more extra copies of a gene associated with ovarian cancer (e.g., one or more extra copies of the HER2 gene). In some embodiments, the individual is HER2 positive. In some embodiments, the individual is HER2 negative. In some embodiments, the ovarian cancer is associated with basal cell nevus (Gorlin) syndrome, multiple endocrine neoplasia type 1 (MEN1), or hereditary nonpolyposis colon cancer (HNPCC).

In some embodiments, the individual satisfies at least two of the criteria described above. For example, in some embodiments, the individual has a measurable disease by RECIST and an elevated blood level of CA-125. In some embodiments, the individual is confirmed of having an ovarian cancer histologically or cytologically and has only been treated with platinum-based agent(s) prior to administration of the nanoparticle compositions described above. In some embodiments, the individual satisfies at least any of two, three, four, five, or more criteria described above. In some embodiments, the individual satisfies all criteria described above.

In some embodiments, the recurrent cancer is platinum sensitive. For example, in some embodiments, the individual has received prior platinum-based chemotherapy and has a treatment-free interval for more than about any of 3, 6, or 9 months since the completion of the platinum-based chemotherapy. In some embodiments, the individual has received prior platinum-based chemotherapy and has a treatment-free interval for more than about any of 12, 18, 24, 36, or 48 months since the completion of the platinum-based chemotherapy. In some embodiments, the recurrent cancer is a platinum-sensitive ovarian cancer. In some embodiments, the recurrent cancer is a platinum-sensitive peritoneal cancer. In some embodiments, the recurrent cancer is a platinum-sensitive fallopian tube cancer.

In some embodiments, the recurrent cancer (such as a recurrent ovarian, peritoneal, or fallopian tube cancer) is platinum resistant. By "platinum-resistant" cancer is meant that the individual with cancer has progressed while receiving platinum-based chemotherapy (i.e. the patient is "platinum refractory").

By "platinum-based chemotherapy" is intended to mean therapy with one or more platinum-based chemotherapeutic agents, optionally in combination with one or more other chemotherapeutic agents. A "platinum-based chemotherapeutic agent" comprises an organic compound which contains platinum as an integral part of the molecule. These agents are believed to inhibit cell growth by forming reactive platinum complexes which form intrastrand and interstrand cross-linking of DNA molecules and inhibit DNA synthesis. Examples of platinum-based chemotherapeutic agents include carboplatin, cisplatin, and oxaliplatinum. In some embodiments, the platinum-based chemotherapy comprises treatment with only platinum-based agents. In some embodiments, the platinum-based chemotherapy comprises treatment with carboplatin.

Dosing and Method of Administration

The amount of the inventive composition administered to an individual (such as a human) may vary with the particular composition, the method of administration, and the particular type of recurrent cancer being treated. The amount should be sufficient to produce a desirable beneficial effect. For example, in some embodiments, the amount of the composition is effective to result in an objective response (such as a partial response or a complete response). In some embodiments, the amount of the taxane nanoparticle composition is sufficient to result in a complete response in the individual. In some embodiments, the amount of the taxane nanoparticle composition is sufficient to result in a partial response in the individual. In some embodiments, the amount of the taxane nanoparticle composition administered (for example when administered alone) is sufficient to produce an overall response rate of more than about any of 40%, 50%, 60%, or 64% among a population of individuals treated with the taxane nanoparticle composition. Responses of an individual to the treatment of the methods described herein can be determined, for example, based on RECIST or CA-125 level. For example, when CA-125 is used, a complete response can be defined as a return to a normal range value of at least 28 days from the pretreatment value. A particle response can be defined as a sustained over 50% reduction from the pretreatment value.

In some embodiments, the amount of the composition is sufficient to prolong progress-free survival of the individual (for example as measured by RECIST or CA-125 changes). In some embodiments, the amount of the composition is sufficient to prolong overall survival of the individual. In some embodiments, the amount of the composition (for example when administered along) is sufficient to produce clinical benefit of more than about any of 50%, 60%, 70%, or 77% among a population of individuals treated with the taxane nanoparticle composition.

In some embodiments, the amount of the taxane (e.g., paclitaxel) in the composition is below the level that induces a toxicological effect (i.e., an effect above a clinically acceptable level of toxicity) or is at a level where a potential side effect can be controlled or tolerated when the composition is administered to the individual. In some embodiments, the amount of the composition is close to a maximum tolerated dose (MTD) of the composition following the same dosing regime. In some embodiments, the amount of the composition is more than about any of 80%, 90%, 95%, or 98% of the MTD.

In some embodiments, the amount of a taxane (e.g., paclitaxel) in the composition is included in any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of a taxane (e.g., paclitaxel) or derivative thereof in the effective amount of the composition (e.g., a unit dosage form) is in the range of about 5 mg to about 500 mg, such as about 30 mg to about 300 mg or about 50 mg to about 200 mg. In some embodiments, the concentration of the taxane (e.g., paclitaxel) in the composition is dilute (about 0.1 mg/ml) or concentrated (about 100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of the taxane (e.g., paclitaxel) is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

Exemplary effective amounts of a taxane (e.g., paclitaxel) in the nanoparticle composition include, but are not limited to, about any of 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 125 mg/m$^2$, 150 mg/m$^2$, 160 mg/m$^2$, 175 mg/m$^2$, 180 mg/m$^2$, 200 mg/m$^2$, 210 mg/m$^2$, 220 mg/m$^2$, 250 mg/m$^2$, 260 mg/m$^2$, 300 mg/m$^2$, 350 mg/m$^2$, 400 mg/m$^2$, 500 mg/m$^2$, 540 mg/m$^2$, 750 mg/m$^2$, 1000 mg/m$^2$, or 1080 mg/m$^2$ of a taxane (e.g., paclitaxel). In various embodiments, the composition includes less than about any of 350 mg/m$^2$, 300 mg/m$^2$, 250 mg/m$^2$, 200 mg/m$^2$, 150 mg/m$^2$, 120 mg/m$^2$, 100 mg/m$^2$, 90 mg/m$^2$, 50 mg/m$^2$, or 30 mg/m$^2$ of a taxane (e.g., paclitaxel). In some embodiments, the amount of the taxane (e.g., paclitaxel) per administration is less than about any of 25 mg/m$^2$, 22 mg/m$^2$, 20 mg/m$^2$, 18 mg/m$^2$, 15 mg/m$^2$, 14 mg/m$^2$, 13 mg/m$^2$, 12 mg/m$^2$, 11 mg/m$^2$, 10 mg/m$^2$, 9 mg/m$^2$, 8 mg/m$^2$, 7 mg/m$^2$, 6 mg/m$^2$, 5 mg/m$^2$, 4 mg/m$^2$, 3 mg/m$^2$, 2 mg/m$^2$, or 1 mg/m$^2$. In some embodiments, the effective amount of a taxane (e.g., paclitaxel) in the composition is included in any of the following ranges: about 1 to about 5 mg/m$^2$, about 5 to about 10 mg/m$^2$, about 10 to about 25 mg/m$^2$, about 25 to about 50 mg/m$^2$, about 50 to about 75 mg/m$^2$, about 75 to about 100 mg/m$^2$, about 100 to about 125 mg/m$^2$, about 125 to about 150 mg/m$^2$, about 150 to about 175 mg/m$^2$, about 175 to about 200 mg/m$^2$, about 200 to about 225 mg/m$^2$, about 225 to about 250 mg/m$^2$, about 250 to about 300 mg/m$^2$, about 300 to about 350 mg/m$^2$, or about 350 to about 400 mg/m$^2$. Preferably, the effective amount of a taxane (e.g., paclitaxel) in the composition is about 5 to about 300 mg/m$^2$, such as about 100 to about 150 mg/m$^2$, about 120 mg/m$^2$, about 130 mg/m$^2$, or about 140 mg/m$^2$.

In some embodiments of any of the above aspects, the effective amount of a taxane (e.g., paclitaxel) in the composition includes at least about any of 1 mg/kg, 2.5 mg/kg, 3.5 mg/kg, 5 mg/kg, 6.5 mg/kg, 7.5 mg/kg, 10 mg/kg, 15 mg/kg, or 20 mg/kg. In various embodiments, the effective amount of a taxane (e.g., paclitaxel) in the composition includes less than about any of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg of a taxane (e.g., paclitaxel).

Exemplary dosing frequencies include, but are not limited to, weekly without break; weekly, three out of four weeks; once every three weeks; once every two weeks; weekly, two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

The administration of the composition can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months. In some embodiments, the taxane (e.g., paclitaxel) or derivative thereof is administered over a period of at least one month, wherein the interval between each administration is no more than about a week, and wherein the dose of the taxane (e.g., paclitaxel) at each administration is about 0.25 mg/m$^2$ to about 75 mg/m$^2$, such as about 0.25 mg/m$^2$ to about 25 mg/m$^2$ or about 25 mg/m$^2$ to about 50 mg/m$^2$.

In some embodiments, the dosage of a taxane (e.g., paclitaxel) in a nanoparticle composition can be in the range of 5-400 mg/m$^2$ when given on a 3 week schedule, or 5-250 mg/m$^2$ when given on a weekly schedule. For example, the amount of a taxane (e.g., paclitaxel) is about 60 to about 300 mg/m$^2$ (e.g., about 260 mg/m$^2$).

Other exemplary dosing schedules for the administration of the nanoparticle composition (e.g., paclitaxel/albumin nanoparticle composition) include, but are not limited to, 100 mg/m$^2$, weekly, without break; 75 mg/m$^2$ weekly, 3 out of four weeks; 100 mg/m$^2$, weekly, 3 out of 4 weeks; 125 mg/m$^2$, weekly, 3 out of 4 weeks; 125 mg/m$^2$, weekly, 2 out of 3 weeks; 130 mg/m$^2$, weekly, without break; 175 mg/m$^2$, once every 2 weeks; 260 mg/m$^2$, once every 2 weeks; 260 mg/m$^2$, once every 3 weeks; 180-300 mg/m$^2$, every three weeks; 60-175 mg/m$^2$, weekly, without break; 20-150 mg/m$^2$ twice a week; and 150-250 mg/m$^2$ twice a week. The dosing frequency of the composition may be adjusted over the course of the treatment based on the judgment of the administering physician.

In some embodiments, the individual is treated for at least about any of one, two, three, four, five, six, seven, eight, nine, or ten treatment cycles.

The compositions described herein allow infusion of the composition to an individual over an infusion time that is shorter than about 24 hours. For example, in some embodiments, the composition is administered over an infusion period of less than about any of 24 hours, 12 hours, 8 hours, 5 hours, 3 hours, 2 hours, 1 hour, 30 minutes, 20 minutes, or 10 minutes. In some embodiments, the composition is administered over an infusion period of about 30 minutes.

In some embodiments, the invention provides a method of treating cancer in an individual by parenterally administering to the individual (e.g., a human) an effective amount of a composition comprising nanoparticles that comprise a taxane (e.g., paclitaxel) and a carrier protein (e.g., albumin such as human serum albumin). The invention also provides a method of treating cancer in an individual by intravenous, intra-arterial, intramuscular, subcutaneous, inhalation, oral, intraperitoneal, nasally, or intra-tracheal administering to the individual (e.g., a human) an effective amount of a composition comprising nanoparticles that comprise a taxane (e.g., paclitaxel) and a carrier protein (e.g., albumin such as human serum albumin). In some embodiments, the route of administration is intraperitoneal. In some embodiments, the route of administration is intravenous, intra-arterial, intramuscular, or subcutaneous. In various embodiments, about 5 mg to about 500 mg, such as about 30 mg to about 300 mg or about 50 to about 500 mg, of the taxane (e.g., paclitaxel) or derivative thereof is administered per dose. In some embodiments, the taxane (e.g., paclitaxel) or derivative thereof is the only pharmaceutically active agent for the treatment of cancer that is contained in the composition. In some embodiments, the method comprises intraperitoneally administering composition comprising nanoparticles that comprise a taxane (e.g., paclitaxel) and a carrier protein (e.g., albumin such as human serum albumin) at the dose of any of about 60 mg/m$^2$, 80 mg/m$^2$, 100 mg/m$^2$, 125 mg/m$^2$, and 150 mg/m$^2$.

Any of the compositions described herein can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In some embodiments, sustained continuous release formulation of the composition may be used. In one variation of the invention, nanoparticles (such as albumin nanoparticles) of the inventive compounds can be administered by any acceptable route including, but not limited to, orally, intramuscularly, transdermally, intravenously, through an inhaler or other air borne delivery systems and the like.

In some embodiments, paclitaxel-containing nanoparticles composition may be administered with a second therapeutic compound and/or a second therapy. The dosing frequency of the paclitaxel-containing nanoparticles composition and the second compound may be adjusted over the course of the treatment based on the judgment of the administering physician. In some embodiments, the first and second therapies are administered simultaneously, sequentially, or concurrently. When administered separately, the taxane (e.g., paclitaxel)-containing nanoparticles composition and the second compound can be administered at different dosing frequency or intervals. For example, the taxane (e.g., paclitaxel)-containing nanoparticle composition can be administered weekly, while a second compound can be administered more or less frequently. In some embodiments, sustained continuous release formulation of the taxane (e.g., paclitaxel)-containing nanoparticle and/or second compound may be used. Various formulations and devices for achieving sustained release are known in the art. A combination of the administration configurations described herein can be used.

When the taxane nanoparticle compositions are administered in conjunction with another chemotherapeutic agent, the nanoparticle composition and the other chemotherapeutic agent can be administered using the same route of administration or different routes of administration. In some embodiments (for both simultaneous and sequential administrations), the taxane in the nanoparticle composition and the other chemotherapeutic agent are administered at a predetermined ratio. For example, in some embodiments, the ratio by weight of the taxane in the nanoparticle composition and the other chemotherapeutic agent is about 1 to 1. In some embodiments, the weight ratio may be between about 0.001 to about 1 and about 1000 to about 1, or between about 0.01 to about 1 and 100 to about 1. In some embodiments, the ratio by weight of the taxane in the nanoparticle composition and the other chemotherapeutic agent is less than about any of 100:1, 50:1, 30:1, 10:1, 9:1, 8:1, 7:1, 6:1, 5:1, 4:1, 3:1, 2:1, and 1:1. In some embodiments, the ratio by weight of the taxane in the nanoparticle composition and the other chemotherapeutic agent is more than about any of 1:1, 2:1, 3:1, 4:1, 5:1, 6:1, 7:1, 8:1, 9:1, 30:1, 50:1, 100:1. Other ratios are contemplated.

The doses required for the taxane and/or the other chemotherapeutic agent may (but not necessarily) be lower than what is normally required when each agent is administered alone. Thus, in some embodiments, a subtherapeutic amount of the drug in the nanoparticle composition and/or the other chemotherapeutic agent are administered. "Subtherapeutic amount" or "subtherapeutic level" refer to an amount that is less than the therapeutic amount, that is, less than the amount normally used when the drug in the nanoparticle composition and/or the other chemotherapeutic agent are administered alone. The reduction may be reflected in terms of the amount administered at a given administration and/or the amount administered over a given period of time (reduced frequency).

In some embodiments, enough chemotherapeutic agent is administered so as to allow reduction of the normal dose of the drug in the nanoparticle composition required to effect the same degree of treatment by at least about any of 5%, 10%, 20%, 30%, 50%, 60%, 70%, 80%, 90%, or more. In some embodiments, enough drug in the nanoparticle composition is administered so as to allow reduction of the normal dose of the other chemotherapeutic agent required to effect the same degree of treatment by at least about any of 5%, 10%, 20%, 30%, 50%, 60%, 70%, 80%, 90%, or more.

In some embodiments, the dose of both the taxane in the nanoparticle composition and the other chemotherapeutic agent are reduced as compared to the corresponding normal dose of each when administered alone. In some embodiments, both the taxane in the nanoparticle composition and the other chemotherapeutic agent are administered at a subtherapeutic, i.e., reduced, level. In some embodiments, the dose of the nanoparticle composition and/or the other chemotherapeutic agent is substantially less than the established maximum toxic dose (MTD). For example, the dose of the nanoparticle composition and/or the other chemotherapeutic agent is less than about 50%, 40%, 30%, 20%, or 10% of the MTD.

Metronomic Therapy Regimes

The present invention also provides metronomic therapy regimes for any of the methods of treatment and methods of administration described herein. Exemplary metronomic therapy regimes and embodiments for the use of metronomic therapy regimes are discussed below and disclosed in U.S. Ser. No. 11/359,286, filed Feb. 21, 2006, published as U.S. Pub. No. 2006/0263434 (such as those described in paragraphs [0138] to [0157]), which is hereby incorporated by reference in its entirety. In some embodiments, the nanoparticle composition is administered over a period of at least one month, wherein the interval between each administration is no more than about a week, and wherein the dose of the taxane (e.g., paclitaxel) at each administration is about 0.25% to about 25% of its maximum tolerated dose following a traditional dosing regime. In some embodiments, the nanoparticle composition is administered over a period of at least two months, wherein the interval between each administration is no more than about a week, and wherein the dose of the taxane (e.g., paclitaxel) at each administration is about 1% to about 20% of its maximum tolerated dose following a traditional dosing regime. In some embodiments, the dose of a taxane (e.g., paclitaxel) per administration is less than about any of 25%, 24%, 23%, 22%, 20%, 18%, 15%, 14%, 13%, 12%, 11%, 10%, 9%, 8%, 7%, 6%, 5%, 4%, 3%, 2%, or 1% of the maximum tolerated dose. In some embodiments, any nanoparticle composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, the composition is administered over a period of at least about any of 2, 3, 4, 5, 6, 7, 8, 9, 10, 11, 12, 18, 24, 30, 36, 48, 60, 72, or 84 months.

Carrier Proteins

Provided herein are also compositions comprising nanoparticles that comprise a taxane and a carrier protein for use in methods of treatment, methods of administration, and dosage regimes described herein. In some embodiments, the carrier protein is albumin. In some embodiments, the carrier protein is human serum albumin.

Examples of suitable carrier proteins include proteins normally found in blood or plasma, which include, but are not limited to, albumin, immunoglobulin including IgA, lipoproteins, apolipoprotein B, α-acid glycoprotein, β-2-macroglobulin, thyroglobulin, transferin, fibronectin, factor VII, factor VIII, factor IX, factor X, and the like. In some embodiments, the carrier protein is a non-blood protein, such as casein, α-lactalbumin, or β-lactoglobulin. The carrier proteins may either be natural in origin or synthetically prepared. In some embodiments, the pharmaceutical acceptable carrier comprises albumin, such as human serum albumin (HSA). HSA is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Other albumins are contemplated, such as bovine serum albumin. Use of such non-human albumins could be appropriate, for example, in the context of use of these compositions in non-human mammals, such as the veterinary animals (including domestic pets and agricultural animals).

Human serum albumin (HSA) has multiple hydrophobic binding sites (a total of eight for fatty acids, an endogenous ligand of HSA) and binds a diverse set of drugs, especially neutral and negatively charged hydrophobic compounds (Goodman et al., *The Pharmacological Basis of Therapeutics*, $9^{th}$ ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (1981), Vorum, *Dan. Med. Bull.*, 46, 379-99 (1999), Kragh-Hansen, *Dan. Med. Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15 (1992), and Carter et al., *Adv. Protein. Chem.*, 45, 153-203 (1994)).

The carrier protein (e.g., albumin) in the composition generally serves as a carrier for the taxane (e.g., paclitaxel) or derivative thereof, i.e., the carrier protein in the composition makes the taxane (e.g., paclitaxel) or derivative thereof more readily suspendable in an aqueous medium or helps maintain the suspension as compared to compositions not comprising a carrier protein. This can avoid the use of toxic solvents for solubilizing of the taxane (e.g., paclitaxel), and thereby can reduce one or more side effects of administration of the taxane (e.g., paclitaxel) into an individual (e.g., human). In some embodiments, the composition is substantially free (e.g. free) of organic solvents or surfactants. A composition is "substantially free of organic solvent" or "substantially free of surfactant" if the amount of organic solvent or surfactant in the composition is not sufficient to cause one or more side effect(s) in an individual when the composition is administered to the individual. In some embodiments, the nanoparticles in the composition have a solid core. In some embodiments, the nanoparticles in the composition have a core that is not aqueous (i.e., other than aqueous core). In some embodiments, the nanoparticles of the composition lack a polymeric matrix. In some embodiments, the nanoparticles of the composition are filter sterilizable. In some embodiments, the nanoparticles in the composition comprise at least one cross-linked carrier protein. In some embodiments, the nanoparticles in the composition comprise at least ten-percent of carrier protein that is cross-linked.

The taxane (e.g., paclitaxel) is "stabilized" in an aqueous suspension if it remains suspended in an aqueous medium (e.g., without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (e.g., human). Stability of the suspension is generally (but not necessarily) evaluated at storage temperature, such as room temperature (e.g., 20-25° C.) or refrigerated conditions (e.g., 4° C.). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the composition comprises nanoparticles comprising (in various embodiments consisting essentially of) a taxane (e.g., paclitaxel) and a carrier protein. When the taxane (e.g., paclitaxel) is in a liquid form, the particles or nanoparticles are also referred to as droplets or nanodroplets. In some embodiments, taxane is coated with the carrier protein. Particles (such as nanoparticles) of poorly water soluble pharmaceutical agents have been disclosed in, for example, U.S. Pat. Nos. 5,916,596; 6,506,405; and 6,537,579 and also in U.S. Pat. App. Pub. No. 2005/0004002A1.

The amount of carrier protein in the composition described herein will vary depending on the taxane (e.g., paclitaxel) or derivative thereof, and other components in the composition. In some embodiments, the composition comprises a carrier protein in an amount that is sufficient to stabilize the taxane (e.g., paclitaxel) in an aqueous suspension, for example, in the form of a stable colloidal suspension (e.g., a stable suspension of nanoparticles). In some embodiments, the carrier protein is in an amount that reduces the sedimentation rate of the taxane (e.g., paclitaxel) in an aqueous medium. The amount of the carrier protein also depends on the size and density of particles of the taxane (e.g., paclitaxel).

In some embodiments of any of the aspects of the invention, the taxanes in the nanoparticles are coated with a carrier protein, such as albumin (e.g., human serum albumin). In some embodiments, the taxane is paclitaxel. In various embodiments, the composition comprises more than about any of 50%, 60%, 70%, 80%, 90%, 95%, or 99% of the taxane or derivative thereof in nanoparticle form. In some embodiments, the taxane or derivative thereof constitutes more than about any of 50%, 60%, 70%, 80%, 90%, 95%, or 99% of the nanoparticles by weight. In some embodiments, the nanoparticles are substantially free of polymeric core materials. In some embodiments, the taxane in the nanoparticles is amorphous. In some embodiments, the taxane used for making the nanoparticle compositions is in anhydrous form. In some embodiments, the carrier protein (such as albumin) to a taxane weight ratio in the taxane nanoparticle composition is about any of 18:1 or less, 15:1 or less, 14:1 or less, 13:1 or less, 12:1 or less, 11:1 or less, 10:1 or less, 9:1 or less, 8:1 or less, 7.5:1 or less, 7:1 or less, 6:1 or less, 5:1 or less, 4:1 or less, or 3:1 or less. In some embodiments, the albumin to taxane weight ratio is between about any of 18:1 to 1:18, 10:1 to 1:10, 9:1 to 1:1, 8:1 to 1:1, 7.5:1 to 1.1, 7.1:1 to 1:1, 6:1 to 1:1, 5:1 to 1:1, 4:1 to 1:1, or 3:1 to 1:1. In some embodiments, the composition comprises a stable aqueous suspension of particles (e.g., nanoparticles) comprising a taxane and carrier protein (such as albumin, e.g., particles of paclitaxel coated with albumin).

In some embodiments, the composition comprises nanoparticles of any shape (e.g., a spherical or non-spherical shape) with an average or mean diameter of no greater than about 1000 nanometers (nm), such as no greater than about any of 900 nm, 800 nm, 700 nm, 600 nm, 500 nm, 400 nm, 300 nm, 200 nm, 100 nm, 90 nm, 80 nm, 70 nm, 60 nm, or 50 nm. In some embodiments, the average or mean diameter of the particles is no greater than about 200 nm. In some embodiments, the composition is sterile filterable. In some embodiments, the composition is sterile filtered. In some embodiments, the average or mean diameter of the particles is no greater than about 100 nm. In some embodiments, the average or mean diameter of the particles is between about 20 to about 400 nm. In some embodiments, the average or mean diameter of the particles is between about 40 to about 200 nm. In some embodiments, the particles are sterile-filterable. In some embodiments, the composition comprises nanoparticles with a diameter of about any of 1000 nm, 900 nm, 800 nm, 700 nm, 600 nm, 500 nm, 400 nm, 300 nm, 200 nm, 100 nm, 90 nm, 80 nm, 70 nm, 60 nm, or 50 nm. In some embodiments, the composition comprises nanoparticles with a diameter of between about any of 50 nm and 150 nm, 50 nm and 75 nm, 50 nm and 100 nm, 75 nm and 100 nm, 100 nm and 125 nm, 125 nm and 150 nm, 100 nm and 150 nm, 150 nm and 175 nm, or 175 nm and 200 nm. In some embodiments, the diameter of about any of 50% or more, 65% or more, 75% or more, 80% or more, 90% or more, 95% or more, 98% or more, 99% or more, 99.5% or more, or 99.9% or more of the nanoparticles can fall within the range specified. Average or mean diameters of nanoparticles can be determined by methods known in the art, for example laser light scattering.

The nanoparticles described herein may be present in a dry formulation (e.g., lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

In some embodiments, the nanoparticles do not comprise a blood-insoluble gas or do not comprise gas-filled microbubbles.

In some embodiments, the carrier protein is present in an effective amount to reduce one or more side effects associated with administration of taxane to a human compared to compositions without carrier protein. These side effects include, but are not limited to, myelosuppression, neurotoxicity, hypersensitivity, inflammation, venous irritation, phlebitis, pain, skin irritation, neutropenic fever, anaphylactic reaction, hematologic toxicity, and cerebral or neurologic toxicity, and combinations thereof. In some embodiments, there is provided a method of reducing hypersensitivity reactions associated with administration of the taxane (e.g., paclitaxel), including, for example, severe skin rashes, hives, flushing, dyspnea, tachycardia, pulmonary hypertension (e.g., lymphoma); chest pain; black, tarry stools; general feeling of illness, shortness of breath; swollen glands; weight loss; yellow skin and eyes, abdominal pain; unexplained anxiousness; bloody or cloudy urine; bone pain; chills; confusion; convulsions (seizures); cough; decreased urge to urinate; fast, slow, or irregular heartbeat; fever; frequent urge to urinate; increased thirst; loss of appetite; lower back or side pain; mood changes; muscle pain or cramps; nausea or vomiting; numbness or tingling around lips, hands, or feet; painful or difficult urination; rash; sore throat; sores or white spots on lips or in mouth; swelling of hands, ankles, feet, or lower legs; swollen glands; trouble breathing; unusual bleeding or bruising; unusual tiredness or weakness; weakness or heaviness of legs, skin ulcer or sores, weight gain, acne; constipation; diarrhea; difficulty in moving; headache; loss of energy or weakness; muscle pain or stiffness; pain; shaking or trembling; trouble sleeping; nosebleed; and/or swelling of the face. These side effects, however, are merely exemplary and other side effects, or combination of side effects, associated with the taxane (e.g., paclitaxel) can be reduced. The side effects may be immediate or delayed (such as not occurring for a few days, weeks, months, or years after treatment begins).

Antimicrobial Agents in Compositions

In some embodiments, the compositions of the invention also includes an antimicrobial agent (e.g., an agent in addition to the taxane (e.g., paclitaxel)) in an amount sufficient to significantly inhibit (e.g., delay, reduce, slow, and/or prevent) microbial growth in the composition for use in the methods of treatment, methods of administration, and dosage regimes described herein. Exemplary microbial agents and variations for the use of microbial agents are disclosed in U.S. Ser. No. 11/514,030, filed Aug. 30, 2006 (such as those described in paragraphs [0036] to [0058]). In some embodiments, the antimicrobial agent is a chelating agent, such as EDTA, edetate, citrate, pentetate, tromethamine, sorbate, ascorbate, derivatives thereof, or mixtures thereof. In some embodiments, the antimicrobial agent is a polydentate chelating agent. In some embodiments, the antimicrobial agent is a non-chelating agent, such as any of sulfites, benzoic acid, benzyl alcohol, chlorobutanol, and paraben. In some embodiments, an antimicrobial other than the taxane discussed above is not contained or used in the methods of treatment, methods of administration, and dosage regimes described herein.

Sugar Containing Compositions

In some embodiments, the compositions of the invention include a sugar for use in the methods of treatment described herein. In some embodiments, the compositions of the invention include both a sugar and an antimicrobial agent for use in the methods of treatment described herein. Exemplary sugars and variations for the use of sugars are disclosed in U.S. Ser. No. 11/514,030, filed Aug. 30, 2006 (such as those described in paragraphs [0084] to [0090]). In some embodiments, the sugar serves as a reconstitution enhancer which causes a lyophilized composition to dissolve or suspend in water and/or aqueous solution more quickly than the lyophilized composition would dissolve without the sugar. In some embodiments, the composition is a liquid (e.g., aqueous) composition obtained by reconstituting or resuspending a dry composition. In some embodiments, the concentration of sugar in the composition is greater than about 50 mg/ml. In some embodiments, the sugar is in an amount that is effective to increase the stability of the taxane (e.g., paclitaxel) or derivative thereof in the composition as compared to a composition without the sugar. In some embodiments, the sugar is in an amount that is effective to improve filterability of the composition as compared to a composition without the sugar.

The sugar-containing compositions described herein may further comprise one or more antimicrobial agents, such as the antimicrobial agents described herein or in U.S. Ser. No. 11/514,030, filed Aug. 30, 2006. In addition to one or more sugars, other reconstitution enhancers (such as those described in U.S. Pat. App. Publication No. 2005/0152979, which is hereby incorporated by reference in its entirety) can also be added to the compositions. In some embodiments, a sugar is not contained or used in the methods of treatment, methods of administration, and dosage regimes described herein.

Stabilizing Agents in Compositions

In some embodiments, the compositions of the invention also include a stabilizing agent for use in the methods of treatment, methods of administration, and dosage regimes described herein. In some embodiments, the compositions of the invention include an antimicrobial agent and/or a sugar and/or a stabilizing agent for use in the methods of treatment, methods of administration, and dosage regimes described herein. Exemplary stabilizing agents and variations for the use of stabilizing agents are disclosed in U.S. Ser. No. 11/513,756, filed Aug. 30, 2006 (such as those described in paragraphs [0038] to [0083] and [0107] to [0114]). The present invention in another variation provides for compositions and methods of preparation of a taxane (e.g., paclitaxel) which retain the desirable therapeutic effects and remain physically and/or chemically stable upon exposure to certain conditions such as prolonged storage, elevated temperature, or dilution for parenteral administration. The stabilizing agent includes, for example, chelating agents (e.g., citrate, malic acid, edetate, or pentetate), sodium pyrophosphate, and sodium gluconate. In some embodiments, the invention provides pharmaceutical formulations of a taxane (e.g., paclitaxel) comprising citrate, sodium pyrophosphate, EDTA, sodium gluconate, citrate and sodium chloride, and/. In another variation, the invention provides a composition of a taxane, wherein the taxane (e.g., paclitaxel) used for preparing the formulation is in an anhydrous form prior to being incorporated into the composition.

In some embodiments, a stabilizing agent is not contained or used in the methods of treatment, methods of administration, and dosage regimes described herein.

Pharmaceutical Compositions and Formulations

The compositions described herein may be used in the preparation of a formulation, such as a pharmaceutical formulation, by combining the nanoparticle composition(s) described with a pharmaceutical acceptable carrier, excipients, stabilizing agents or other agent, which are known in the art, for use in the methods of treatment, methods of administration, and dosage regimes described herein. To increase stability by increasing the negative zeta potential of nanoparticles, certain negatively charged components may be added. Such negatively charged components include, but are not limited to bile salts, bile acids, glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid, and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine, stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearoylphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. There are a wide variety of suitable formulations of the inventive composition (see, e.g., U.S. Pat. Nos. 5,916,596 and 6,096,331, which are hereby incorporated by reference in their entireties). The following formulations and methods are merely exemplary and are in no way limiting. Formulations suitable for oral administration can comprise (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, (d) suitable emulsions, and (e) powders. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizing agents, and preservatives. The formulations can be presented in unit-dose or multi-dose sealed containers, such as ampules and vials, and can be stored in a freeze-dried (lyophilized) condition requiring only the addition of the sterile liquid excipient methods of treatment, methods of administration, and dosage regimes described herein (i.e., water) for injection, immediately prior to use. Extemporaneous injection solutions and suspensions can be prepared from sterile powders, granules, and tablets of the kind previously described. Injectable formulations are preferred.

The invention also includes formulations of nanoparticle compositions comprising the taxane (e.g., paclitaxel) or derivative thereof and a carrier suitable for administration by inhalation for use in the methods of the invention. Formulations suitable for aerosol administration comprise the inventive composition include aqueous and non-aqueous, isotonic sterile solutions, which can contain anti-oxidants, buffers, bacteriostats, and solutes, as well as aqueous and non-aqueous sterile suspensions that can include suspending agents, solubilizers, thickening agents, stabilizing agents, and preservatives, alone or in combination with other suitable components, which can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

In some embodiments, the composition is formulated to have a pH in the range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (e.g., about 8). The composition can also be made to be isotonic with blood by the addition of a suitable tonicity modifier, such as glycerol.

The nanoparticles of this invention can be enclosed in a hard or soft capsule, can be compressed into tablets, or can be incorporated with beverages or food or otherwise incorporated into the diet. Capsules can be formulated by mixing the nanoparticles with an inert pharmaceutical diluent and inserting the mixture into a hard gelatin capsule of the appropriate size. If soft capsules are desired, a slurry of the nanoparticles with an acceptable vegetable oil, light petroleum or other inert oil can be encapsulated by machine into a gelatin capsule.

Also provided are unit dosage forms comprising the compositions and formulations described herein. These unit dosage forms can be stored in a suitable packaging in single or multiple unit dosages and may also be further sterilized and sealed. For example, the pharmaceutical composition (e.g., a dosage or unit dosage form of a pharmaceutical composition) may include (i) nanoparticles that comprise a taxane (e.g., paclitaxel) and a carrier protein and (ii) a pharmaceutically acceptable carrier. In some embodiments, the pharmaceutical composition also includes one or more other compounds (or pharmaceutically acceptable salts thereof) that are useful for treating cancer. In various embodiments, the amount of a taxane (e.g., paclitaxel) in the composition is included in any of the following ranges: about 5 to about 50 mg, about 20 to about 50 mg, about 50 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of a taxane (e.g., paclitaxel) or derivative thereof in the composition (e.g., a dosage or unit dosage form) is in the range of about 5 mg to about 500 mg, such as about 30 mg to about 300 mg or about 50 mg to about 200 mg, of the taxane (e.g., paclitaxel) or derivative thereof. In some embodiments, the carrier is suitable for parental administration (e.g., intravenous administration). In some embodiments, the taxane (e.g., paclitaxel) or derivative thereof is the only pharmaceutically active agent for the treatment of cancer that is contained in the composition.

In some embodiments, the invention features a dosage form (e.g., a unit dosage form) for the treatment of cancer comprising (i) nanoparticles that comprise a carrier protein and a taxane (e.g., paclitaxel), wherein the amount of a taxane (e.g., paclitaxel) or derivative thereof in the unit dosage from is in the range of about 5 mg to about 500 mg, and (ii) a pharmaceutically acceptable carrier. In some embodiments, the amount of the taxane (e.g., paclitaxel) or derivative thereof in the unit dosage form includes about 30 mg to about 300 mg.

Also provided are articles of manufacture comprising the compositions, formulations, and unit dosages described herein in suitable packaging for use in the methods of treatment, methods of administration, and dosage regimes described herein. Suitable packaging for compositions described herein are known in the art, and include, for example, vials (such as sealed vials), vessels (such as sealed vessels), ampules, bottles, jars, flexible packaging (e.g., sealed Mylar or plastic bags), and the like. These articles of manufacture may further be sterilized and/or sealed.

Kits

The invention also provides kits comprising the compositions, formulations, unit dosages, and articles of manufacture described herein for use in the methods of treatment, methods of administration, and dosage regimes described herein. Kits of the invention include one or more containers comprising a taxane (e.g., paclitaxel)-containing nanoparticle compositions (formulations or unit dosage forms and/or articles of manufacture), and in some embodiments, further comprise instructions for use in accordance with any of the methods of treatment described herein. In some embodiments, the kit comprises i) a composition comprising nanoparticles comprising a taxane (e.g., paclitaxel) and a carrier protein (such as albumin) and ii) instructions for administering the nanoparticles and the other chemotherapeutic agents simultaneously and/or sequentially, for treatment of cancer. In various embodiments, the amount of a taxane (e.g., paclitaxel) in the kit is included in any of the following ranges: about 5 mg to about 20 mg, about 20 to about 50 mg, about 50 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of a taxane (e.g., paclitaxel) in the kit is in the range of about 5 mg to about 500 mg, such as about 30 mg to about 300 mg or about 50 mg to about 200 mg. In some embodiments, the kit includes one or more other compounds (i.e., one or more compounds other than a taxane) that are useful for cancer.

Instructions supplied in the kits of the invention are typically written instructions on a label or package insert (e.g., a paper sheet included in the kit), but machine-readable instructions (e.g., instructions carried on a magnetic or optical storage disk) are also acceptable. The instructions relating to the use of the nanoparticle compositions generally include information as to dosage, dosing schedule, and route of administration for the intended treatment. The kit may further comprise a description of selecting an individual suitable or treatment.

The present invention also provides kits comprising compositions (or unit dosages forms and/or articles of manufacture) described herein and may further comprise instruction(s) on methods of using the composition, such as uses further described herein. In some embodiments, the kit of the invention comprises the packaging described above. In other embodiments, the kit of the invention comprises the packaging described above and a second packaging comprising a buffer. It may further include other materials desirable from a commercial and user standpoint, including other buffers, diluents, filters, needles, syringes, and package inserts with instructions for performing any methods described herein.

For combination therapies of the invention, the kit may contain instructions for administering the first and second therapies simultaneously and/or sequentially for the effective treatment of cancer. The first and second therapies can be present in separate containers or in a single container. It is understood that the kit may comprise one distinct composition or two or more compositions wherein one composition comprises a first therapy and one composition comprises a second therapy.

Kits may also be provided that contain sufficient dosages of the taxane (e.g., paclitaxel) as disclosed herein to provide effective treatment for an individual for an extended period, such as any of a week, 2 weeks, 3 weeks, 4 weeks, 6 weeks, 8 weeks, 3 months, 4 months, 5 months, 6 months, 7 months, 8 months, 9 months or more. Kits may also include multiple unit doses of the taxane (e.g., paclitaxel) compositions, pharmaceutical compositions, and formulations described herein and instructions for use and packaged in quantities sufficient for storage and use in pharmacies, for example, hospital pharmacies and compounding pharmacies. In some embodiments, the kit comprises a dry (e.g., lyophilized) composition that can be reconstituted, resuspended, or rehydrated to form generally a stable aqueous suspension of nanoparticles comprising a taxane (e.g., paclitaxel) and albumin (e.g., a taxane (e.g., paclitaxel) coated with albumin).

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information.

Methods of Making the Compositions

Methods of making compositions containing carrier proteins and poorly water soluble pharmaceutical agents are known in the art. For example, nanoparticles containing poorly water soluble pharmaceutical agents and carrier proteins (e.g., albumin) can be prepared under conditions of high shear forces (e.g., sonication, high pressure homogenization, or the like). These methods are disclosed in, for example, U.S. Pat. Nos. 5,916,596; 6,506,405; and 6,537,579 and also in U.S. Pat. Pub. No. 2005/0004002A1, which are each hereby incorporated by reference in their entireties.

Briefly, the taxane (e.g., paclitaxel) is dissolved in an organic solvent. Suitable organic solvents include, for example, ketones, esters, ethers, chlorinated solvents, and other solvents known in the art. For example, the organic solvent can be methylene chloride, chloroform/ethanol, or chloroform/t-butanol (for example with a ratio of about any of 1:9, 1:8, 1:7, 1:6, 1:5, 1:4, 1:3, 1:2, 1:1, 2:1, 3:1, 4:1, 5:1, 6:1, 7:1, 8:1, or 9:1 or with a ratio of about any of 3:7, 5:7, 4:6, 5:5, 6:5, 8:5, 9:5, 9.5:5, 5:3, 7:3, 6:4, or 9.5:0.5). The solution is added to a carrier protein (e.g., human serum albumin). The mixture is subjected to high pressure homogenization (e.g., using an Avestin, APV Gaulin, Microfluidizer™ such as a Microfluidizer™ Processor M-110EH from Microfluidics, Stansted, or Ultra Turrax homogenizer). The emulsion may be cycled through the high pressure homogenizer for between about 2 to about 100 cycles, such as about 5 to about 50 cycles or about 8 to about 20 cycles (e.g., about any of 8, 10, 12, 14, 16, 18 or 20 cycles). The organic solvent can then be removed by evaporation utilizing suitable equipment known for this purpose, including, but not limited to, rotary evaporators, falling film evaporators, wiped film evaporators, spray driers, and the like that can be operated in batch mode or in continuous operation. The solvent may be removed at reduced pressure (such as at about any of 25 mm Hg, 30 mm Hg, 40 mm Hg, 50 mm Hg, 100 mm Hg, 200 mm Hg, or 300 mm Hg). The amount of time used to remove the solvent under reduced pressure may be adjusted based on the volume of the formulation. For example, for a formulation produced on a 300 mL scale, the solvent can be removed at about 1 to about 300 mm Hg (e.g., about any of 5-100 mm Hg, 10-50 mm Hg, 20-40 mm Hg, or 25 mm Hg) for about 5 to about 60 minutes (e.g., about any of 7, 8, 9, 10, 11, 12, 13, 14, 15, 16, 18, 20, 25, or 30 minutes).

If desired, human albumin solution may be added to the dispersion to adjust the human serum albumin to the taxane (e.g., paclitaxel) ratio or to adjust the concentration of the taxane (e.g., paclitaxel) in the dispersion. For example, human serum albumin solution (e.g., 25% w/v) can be added to adjust the human serum albumin to a taxane (e.g., paclitaxel) ratio to about any of 18:1, 15:1, 14:1, 13:1, 12:1, 11:1, 10:1, 9:1, 8:1, 7.5:1, 7:1, 6:1, 5:1, 4:1, or 3:1. For example, human serum albumin solution (e.g., 25% w/v) or another solution is added to adjust the concentration of a taxane (e.g., paclitaxel) in the dispersion to about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml. The dispersion may be serially filtered through multiple filters, such as a combination of 1.2 μM and 0.8/0.2 μm filters; the combination of 1.2 μm, 0.8 μm, 0.45 μm, and 0.22 μm filters; or the combination of any other filters known in the art. The dispersion obtained can be further lyophilized. The nanoparticle compositions may be made using a batch process or a continuous process (e.g., the production of a composition on a large scale).

If desired, a second therapy (e.g., one or more compounds useful for treating cancer), an antimicrobial agent, sugar, and/or stabilizing agent can also be included in the composition. This additional agent can either be admixed with the taxane (e.g., paclitaxel) and/or the carrier protein during preparation of the taxane (e.g., paclitaxel)/carrier protein composition, or added after the taxane (e.g., paclitaxel)/carrier protein composition is prepared. In some embodiments, the agent is admixed with the taxane (e.g., paclitaxel)/carrier protein composition prior to lyophilization. In some embodiments, the agent is added to the lyophilized pharmaceutical agent/carrier protein composition. In some embodiments when the addition of the agent changes the pH of the composition, the pH in the composition are generally (but not necessarily) adjusted to a desired pH. Exemplary pH values of the compositions include, for example, in the range of about 5 to about 8.5. In some embodiments, the pH of the composition is adjusted to no less than about 6, including for example no less than any of about 6.5, 7, or 8 (e.g., about 8).

Unless defined otherwise, the meanings of all technical and scientific terms used herein are those commonly understood by one of skill in the art to which this invention belongs. One of skill in the art will also appreciate that any methods and materials similar or equivalent to those described herein can also be used to practice or test the invention.

The following Examples are provided to illustrate, but not limit, the invention.

EXAMPLES

The examples, which are intended to be purely exemplary of the invention and should therefore not be considered to limit the invention in any way, also describe and detail aspects and variations of the invention discussed above. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Exemplary Method for the Formation of Nanoparticle Compositions with Paclitaxel and Albumin This example provides formulations of paclitaxel/albumin. The compositions were prepared essentially as described in U.S. Pat. Nos. 5,439,686 and 5,916,596. Briefly, paclitaxel was dissolved in an organic solvent (such as methylene chloride or a chloroform/ethanol mixture), and the solution was added to a human serum albumin solution. The mixture was homogenized for 5 minutes at low RPM to form a crude emulsion, and then transferred into a high pressure homogenizer. The emulsification was performed at 9000-40,000 psi while recycling the emulsion for at least 5 cycles. The resulting system was transferred into a rotary evaporator, and the organic solvent was rapidly removed at 40° C., at reduced pressure (30 mm Hg) for 20-30 minutes. The dispersion was then further lyophilized for 48 hours. The resulting cake was reconstituted to the original dispersion by addition of sterile water or saline, which may optionally contain additional antimicrobial agent(s).

Example 2

Evaluation of Efficacy of Nanoparticle Albumin Bound Paclitaxel (Nab-paclitaxel) in Treating Platinum-Sensitive Patients with Recurrent Ovarian, Peritoneal, or Fallopian Tube Cancer The primary objective of this study was to determine the objective response rate in platinum-sensitive patients with recurrent ovarian, peritoneal, or fallopian tube cancer. The study also evaluated the progression free survival, overall survival, quality of life during treatment, and the safety and toxicity of the treatment in this patient population.

Patient Population Evaluated

Patients were eligible for inclusion for inclusion in this study if she met all of the following criteria: had histologically or cytologically confirmed epithelial cancer of the ovary, fallopian tube or peritoneum (any stage, grade 2-3 if stage 1), had measurable disease by RECIST or elevated CA-125 (>70) in the absence of measurable disease, had received prior platinum-based chemotherapy, was considered platinum sensitive (i.e., having a treatment-free interval >6 months since completion of platinum base chemotherapy), had an ECOG Performance Status (PS) 0-2, had a present, existing peripheral neuropathy which was less than or equal to Grade 1, and had signed an Institutional Review Board approved informed consent. Patients were excluded from this study if she met any of the following criteria: had previously untreated stage 1, Grade 1 disease, was chemotherapy-naïve, had received more than one prior regimen or prior regimen that was not platinum-based, had non-epithelial disease, had nonmeasurable disease with CA-125 less than or equal to 70, had received a taxane within 6 months of registration or any prior treatment with Nab-paclitaxel.

Treatment Schedule

Premedication was administered at the discretion of the treating physician. Patients received 260 mg/m² of Nab-paclitaxel (Abraxane®) administered IV during a 30-minute period on Day 1 of each 21-day cycle. Successive cycles were initiated every 3 weeks and were continued until there was evidence of disease progression, unacceptable toxicity, or until 6 cycles. In patients whose only disease measure was an elevated CA-125, up to 3 cycles of treatment were to be administered at the discretion of the treating physician before response was assessed. Patients who achieved a CR could have received an additional 2 cycles at the discretion of the treating physician therefore, CR patients were eligible to receive a maximum of 8 cycles.

Assessments

Baseline: Complete medical history and physical exam, assessment of ECOG performance status and peripheral neuropathy, CBC, CMP, CA-125, pregnancy test (if appropriate), clinical and radiological assessment of the sites of disease, urinalysis, ECG, and completion FACT-O quality of life questionnaire was determined.

During treatment (prior to the start of each cycle): brief medical history and physical exam, assessment of ECOG performance status and peripheral neuropathy, CBC, CMP, CA-125, pregnancy test (if appropriate), clinical and radiological assessment of tumor response, assessment of other sites of disease, toxicity assessments, and completion FACT-O quality of life questionnaire. These same assessments were made at the time that patients went off study treatment and every 3 months for a total of 18 months after the last dose. Responses were assessed by RECIST criteria, CA-125 criteria, or both. See Therasse P. et al., *J. NCI* 95:205-16 (2000). Response assessment using RECIST followed the commonly applied definitions.

Using CA-125, a complete response was defined as a return to a normal range value for at least 28 days from the pretreatment value. See Rustin et al. *Clin. Cancer Res.* 10(11):3919-26 (2004). A partial response was defined as a sustained over 50% reduction from the pretreatment value. Stable disease was defined as a sustained greater than 50% increase in CA-125 over 28 days in the absence of any new clinically measurable disease, after an adequate trial of therapy. Progressive disease was defined as a sustained over 50% increase in CA-125 or development of new clinically measurable disease after an adequate trial of therapy. An increase was measured from the nadir (the lowest CA-125 value since enrollment).

Patients who discontinued due to adverse events, PD, non-compliance, etc. were followed only for survival, additional therapy, site and date of relapse or progression. Adverse event data were collected for 30 days following last dose.

Patient Characteristics

The majority of enrolled patients had recurrence of disease great than 12 months since prior platinum based chemotherapy.

TABLE 1

Patient characteristics.

| | |
|---|---|
| Number of Subjects Enrolled | 47 |
| Age (Years) | |
| Median | 65.4 |
| Range | 42-84 |

| | Number and Percentage (%) of Subjects |
|---|---|
| Race | |
| White | 41 (87.2) |
| Black | 1 (2.1) |
| Hispanic | 3 (6.4) |
| Asian | 1 (2.1) |
| Indian | 1 (2.1) |

TABLE 1-continued

Patient characteristics.

| | |
|---|---|
| ECOG Performance Status* | |
| 0 | 38 (80.8) |
| 1 | 9 (19.2) |
| Prior Therapy** | |
| Prior Chemotherapy greater than or equal to 12 months | 43 (91.5) |
| Prior Chemotherapy less than or equal to 12 months | 4 (8.5) |
| Surgery | 44 (93.6) |
| Site of Primary Disease | |
| Epithelial ovarian | 37 (78.7) |
| Fallopian tube | 1 (2.1) |
| Peritoneum | 9 (19.2) |
| Histological Grade | |
| GX (can not be assessed) | 1 (2.1) |
| G1 (well differentiated) | 4 (8.5) |
| G2 (moderately differentiated) | 9 (19.2) |
| G3 (poorly differentiated) | 23 (48.9) |
| Missing/Unknown | 10 (21.3) |

*Assessed prior to first treatment
**Subjects may not have more than one prior chemotherapy regimen.

Status

TABLE 2

Patient Status.

| | |
|---|---|
| Total Number of Subjects | 47 |

| | Number and Percentage (%) of Subjects |
|---|---|
| Status | |
| Alive | 44 (93.6) |
| Dead | 3 (6.4) |
| Cause of Death | |
| Progressive disease | 3 |
| Reason for Discontinuation | |
| Normal Completion | 30 (63.8) |
| Toxicity | 1 (2.1) |
| Patient Request/Withdrew Consent | 2 (4.2) |
| Investigator decision | 3 (6.4) |
| Recurrence | 10 (21.3) |
| Other (Coronary artery bypass surgery) | 1 (2.1) |
| Total Cycles Received | |
| Median | 6.0 |
| Range | 1-8 |

Response to Treatment

Figure 1B:
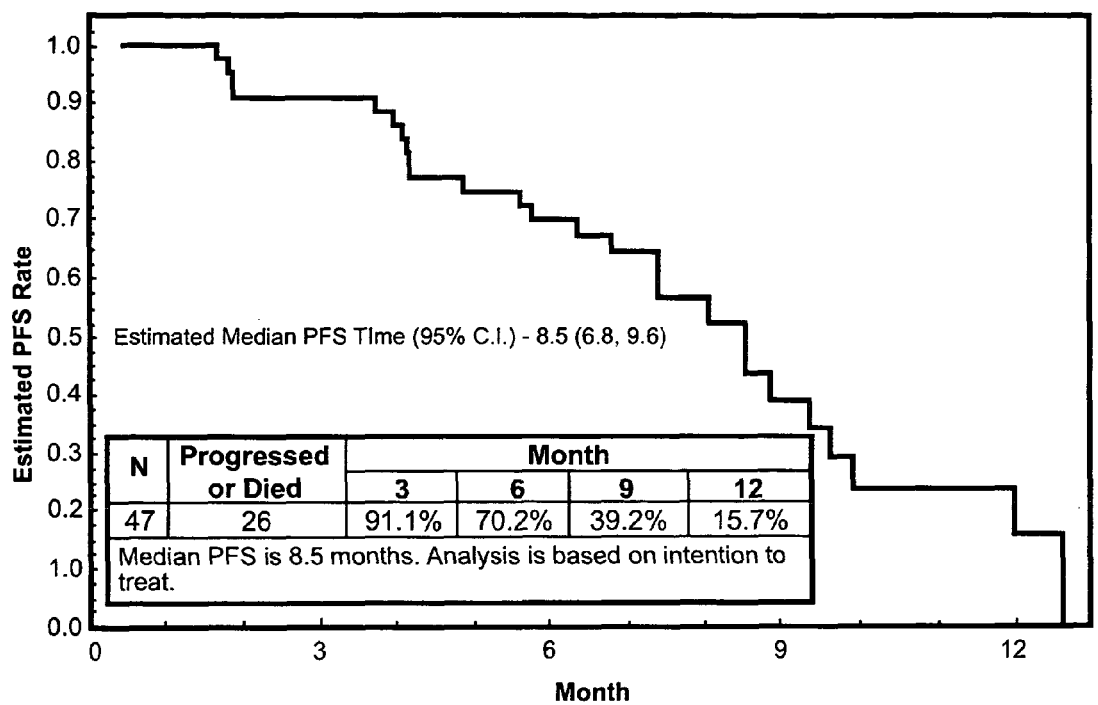
FIG. 1b shows progression free survival among patients plotted in terms of months (x-axis) to proportion not progressed (y-axis).

Overall response rates were calculated using either RECIST or CA-125 or both, the ORR (CP+PR) was 63.2%. Three patients were not evaluable, two were found to be ineligible after start of treatment, and one patient was never treated. Overall survival and progression free survival were plotted in terms of months (x-axis) to proportion of survival or proportion not progressed (y-axis), respectively. See FIGS. 1a and 1b.

TABLE 3

Patient Response

| Total Number of Eligible/Treated Subjects | 44 | |
| --- | --- | --- |
| | N (%) | 95% CI |
| Best Response | | |
| Complete Response | 14 (31.8) | (18.1, 45.6) |
| Partial Response | 14 (31.8) | (18.1, 45.6) |
| Stable disease | 14 (31.8) | (18.1, 45.6) |
| SD greater than or equal to 6 months | 6 | |
| SD less than 6 moths | 8 | |
| Progressive disease | 2 (4.5%) | (0, 10.7) |
| Clinical Benefit | 34 (77.3) | |
| Non-evaluable | 3 | |
| Time to Response (months) | | |
| Median | 1.8 | |
| Range | 0.6-3.4 | |
| Duration of Response (months) | | |
| Median | 6.5 | |
| Range | 2.7-13.2 | |
| 95% CI | 6.6, NA | |

TABLE 4

Best Response.

| Best Response | By RECIST | By CA-125 | By RECIST and CA-125 |
| --- | --- | --- | --- |
| Complete Response | 1 | 6 | 7 |
| Partial Response | 4 | 3 | 7 |
| Stable disease | 5 | 2 | 7 |
| SD greater than or equal to 6 months | 3 | 0 | 3 |
| SD less than 6 moths | 2 | 2 | 4 |
| Progressive disease | 1 | 0 | 1 |
| Clinical Benefit | 8 | 9 | 17 |

Treatment-Related Toxicity >Grade 3

There were 56 patients treated. Grade 3 neuropathy occurred in 8.7% of patients.

TABLE 5

Treatment-related Grade 3-4 Toxicity in greater than or equal to 2% of patients

| Adverse Event | Grade 3 | Grade 4 | Total | Total % |
| --- | --- | --- | --- | --- |
| Hematologic | | | | |
| Leukopenia | 6 | 0 | 6 | 13.0% |
| Neutropenia | 6 | 5 | 11 | 23.9% |
| Nonhematologic | | | | |
| Abdominal pain | 1 | 0 | 1 | 2.2% |
| Diarrhea | 1 | 0 | 1 | 2.2% |
| Fatigue | 1 | 0 | 1 | 2.2% |
| Neuropathy | 4 | 0 | 4 | 8.7% |
| Pneumonia | 1 | 0 | 1 | 2.2% |
| Upper respiratory tract infection | 1 | 0 | 1 | 2.2% |
| Generalized weakness | 1 | 0 | 1 | 2.2% |

TABLE 6

Incidences of Alopecia

| Alopecia | |
| --- | --- |
| Grade 1 | 5 (10.8%) |
| Grade 2 | 35 (76.1%) |

Estimated Quality of Life

The Quality of Life (FACT-O) questionnaire was completed at baseline and before each cycle. Overall quality of life measured decreased from baseline at the initiation of therapy. As measured by the questionnaire, the major contributors to the initial decline in quality of life were the functional, social, and physical well being assessments. All measure improved at the completion of therapy and returned to based line.

Conclusion

Nab-paclitaxel was very active as a single agent in patients with platinum sensitive recurrent ovarian, peritoneal, or fallopian tube cancer. The ORR was 64% and the clinical benefit rate was 77%. Toxicities were tolerable and manageable.

Example 3

Evaluation of Efficacy of Nab-paclitaxel Plus Carboplatin in Treating Patients with Recurrent Platinum-Sensitive Ovarian or Primary Peritoneal Cancer This open-label, non-randomized study was designed to determine the efficacy and safety of nab-paclitaxel (a 130-nm albumin-bound particle form of paclitaxel) plus carboplatin in patients with metastatic ovarian or primary peritoneal carcinoma following platinum-based chemotherapy.

Methods

Eligible patients had to have either measurable disease (based on RECIST criteria) or pretreatment CA-125 levels >2 times the upper limit of normal in the absence of measurable disease. Patients also had to have good performance status, adequate hepatic/renal function, peripheral neuropathy <grade 1, and life expectancy >6 months. Patients may have received prior chemotherapy for ovarian cancer, including taxane-containing regimens, provided the treatment was completed at least 6 months before enrollment. Nab-Paclitaxel 100 mg/m$^2$ was administered IV over 30 minutes on days 1, 8, and 15 every 28 days. Carboplatin AUC 6 was administered IV over 1-2 hours on day 1 every 28 days. Treatment continued for 6 cycles (or longer in the absence of unacceptable toxicity). Planned sample size was 43 patients (39 evaluable). Efficacy was determined by changes in tumor size for patients with measurable disease or changes in CA-125 levels for those with non-measurable disease.

Results

To date, 10 patients have been enrolled, 2 of whom completed 2 treatment cycles; both patients had a 50% reduction in their disease (partial response). One patient had grade 4 neutropenia; grade 3 hematologic events were neutropenia (2 patients), thrombocytopenia (3), and anemia (1). Severe headache and severe nausea were reported for 2 patients each; all 4 events required medication.

Conclusions

Preliminary results indicated that nab-paclitaxel 100 mg/m2 plus carboplatin AUC 6 will have antitumor activity in patients with recurrent platinum-sensitive ovarian or primary peritoneal cancer and that treatment appears to be well tolerated.

Example 3B

Abraxane® Plus Carboplatin in Patients with Recurrent Platinum-Sensitive Ovarian or Primary Peritoneal Cancer: Evaluation of the Response and Survival and Progression-Free Survival The aim of this study was to evaluate the effectiveness of Abraxane® plus carboplatin in the treatment of patients with recurrent platinum-sensitive ovarian or primary peritoneal cancer.

Methods

Patients with recurrent platinum-sensitive ovarian or primary peritoneal carcinoma with measurable or biological evidence of disease had received Abraxane® 100 mg/m² on days 1, 8, and 15 and carboplatin AUC 5 on day 1, every 28 days, intravenously for six cycles. In this study of patients with advanced ovarian cancer, an interim data analysis was conducted of the first 29 of 43 patients who had completed six cycles of treatment. Patients were evaluated with respect to the safety, tolerability, and antitumor effect of intravenous Abraxane® plus carboplatin. Efficacy was measured as changes from baseline in tumor size measured by CT using RECIST Criteria, survival, progression-free survival, and recurrence-free survival during treatment and post study. Safety and tolerability were monitored through adverse events and clinical laboratory values, as well as physical examinations during study drug dosing.

Results

Twenty-six of 29 patients completed six cycles of chemotherapy. Complete response was attained by 20 of 29 (68.9%) patients. Partial response based on CT evaluation was achieved by four of 29 (13.8%) patients. In one of 29 (3.4%) patients, tumor size increased after the second cycle and then decreased. Two of 29 (6.8%) patients progressed and discontinued treatment: one (1/29, 3.4%) discontinued treatment secondary to carboplatin toxicity and the other (1/29, 3.4%) patient discontinued treatment secondary to severe thrombocytopenia. Abraxane® plus carboplatin can be used to treat recurrent platinum-sensitive ovarian or primary peritoneal cancer effectively.

Example 4

Comparison of Pharmacokinetics of Intravenous and Intraperitoneal

The purpose of this study was to compare the pharmacokinetics of intravenous and intraperitoneal administration of Nab-paclitaxel. For intravenous administration, 20 rats were dosed with Abraxane® at 50 mg/kg. Dose volume of 10 ml/kg was delivered intravenously via the tail vein. Blood was drawn at the following intervals for LC/MS/MS analysis of paclitaxel: 0.0, 0.083, 0.25, 0.5, 1, 2, 4, 8, 24, 48, 72 hr. For intraperitoneal administration, 3 rats were dosed with Abraxane® at 50 mg/kg. Dose volume of 10 ml/kg was delivered intraperitoneally. Blood was drawn at the following intervals for LC/MS/MS analysis of paclitaxel: 0.0, 0.083, 0.25, 0.5, 1, 2, 4, 8, 24, 48, 72 hr.

Results

Figure 2:
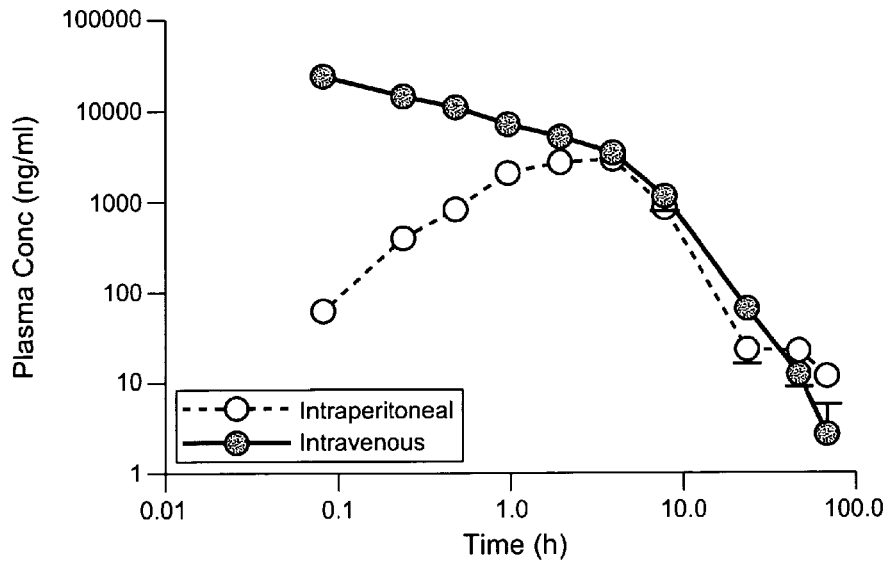
FIG. 2 shows a comparison of plasma level of paclitaxel when Nab-paclitaxel is administered intraperitoneally or intravenously (log-log).
Figure 3:
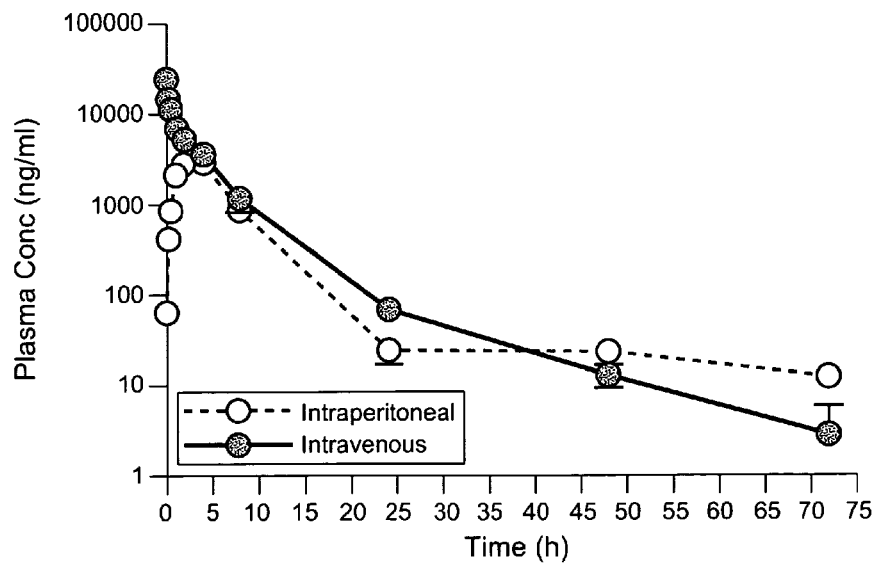
FIG. 3 shows a comparison of plasma level of paclitaxel when Nab-paclitaxel is administered intraperitoneally or intravenously (log-linear).

The plasma level of paclitaxel was measured by LC/MS/MS analysis (FIG. 2 and FIG. 3). As indicated in Table 7, intraperitoneal delivery leaded to a slow absorption of paclitaxel into the circulation with $t_{max}$ occurring at ~3 hrs. The terminal half-lives of paclitaxel when administered intraperitoneally or intravenously were about the same. Systemic exposure after IP administration was ~50% of IV (over 72 hrs), indicating substantial local intraperitoneal exposure of drug, especially in the early phase (0-4 hrs) after administration. There may be sustained exposure beyond 72 hrs; however, this study was terminated at 72 hrs.

TABLE 7

| | Pharmacokinetics Parameters of Intravenous and Intraperitoneal | | | | | | |
|---|---|---|---|---|---|---|---|
| | HL (h) | $T_{max}$ (hr) | $C_{max}$ (ng/ml) | AUC last (hr * ng/ml) | AUC inf (hr * ng/ml) | % AUC Extrapolate | F (%) |
| IP (N = 3) | 6.31 ± 0.20 | 3.33 ± 1.16 | 3207 ± 717 | 26233 ± 3848 | 26770 ± 3904 | 2.0 ± 1.2 | 53 |
| IV (N = 20) | 7.96 ± 4.05 | 0.083 ± 0.000 | 25060 ± 3573 | 50038 ± 6134 | 50146 ± 6137 | 0.2 ± 0.1 | |

Example 5

Intraperitoneal Administration of Abraxane® in Recurrent Mullerian Cancer

Intraperitoneal therapy for recurrent diseases is an area that requires further study. The purpose of this experiment is to determine the safety, efficacy, and maximum tolerable dose of Nab-paclitaxel when administered intraperitoneally.

Methods

A Phase I dose-escalation trial is conducted with 6 patients per cohort to provide sufficient pharmacokinetic data points. Every 4 weeks dosages are escalated so that the cumulative toxicity of weekly treatment may be evaluated. When the MTD is reached, an additional 10 patients are treated to obtain further information about the tolerability at this dose continuously (or ¾ weeks) as well as preliminary information regarding efficacy.

Intraperitoneal dosing of Abraxane® begins at 60 mg/m². Doses is escalated as follows: Dose level 1: 60 mg/m², Dose level 2: 80 mg/m², Dose level 3: 100 mg/m², Dose level 4: 125 mg/m², and Dose level 5: 150 mg/m². Ten patients are added at the DLT, and the study is expected to accrue approximately 30-40 patients.

Patient Population

Patients are included in the study if they meet the following criteria: having recurrent Mullerian cancer (ovarian, peritoneal, fallopian tube, malignant mixed mullerian tumor, serous endo), having disease <1 cm by CT/MRI or SLO, displaying adequate heme/hepatic/renal function, and PS 0-1. Patients are excluded based on meeting the following criteria: having a bowel obstruction (or impending), existing intra-abdominal infection, having significant loculations/adhesions or other contraindications to IP port placement, existing neuropathy >grade 1, having extraperitoneal disease, or displaying an inability to tolerate IV paclitaxel and docetaxel, suggestive of taxane allergy.

What is claimed is:

1. A method of treating a recurrent ovarian, peritoneal, or fallopian tube cancer in an individual, comprising administering to the individual an effective amount of a composition comprising nanoparticles comprising a taxane and a carrier protein, wherein the individual has received a prior chemotherapy and has a treatment free interval for more than about three months prior to the initiation of the treatment, wherein the nanoparticle composition is not administered in conjunction with a platinum-based agent, and wherein the composition comprising nanoparticles comprising a taxane and a carrier protein is administered at a single dose of about 5 mg/m$^2$ to about 400 mg/m$^2$ every three weeks.

2. The method of claim 1, wherein the recurrent ovarian, peritoneal, or fallopian cancer is platinum-sensitive.

3. The method of claim 1, wherein the individual has received a prior platinum-based chemotherapy and has a treatment free interval of more than about 12 months since the completion of the platinum-based chemotherapy.

4. The method of claim 1, wherein the composition comprising nanoparticles comprising a taxane and a carrier protein is administered alone.

5. The method of claim 1, wherein the taxane is paclitaxel.

6. The method of claim 1, wherein the carrier protein is albumin.

7. The method of claim 1, wherein the nanoparticles in the composition have an average or mean diameter of no greater than about 200 nm.

8. The method of claim 7, wherein the composition comprising nanoparticles comprising a taxane and a carrier protein is Nab-paclitaxel.

9. The method of claim 1, wherein the individual has received a prior chemotherapy and has a treatment free interval for more than about 6 months prior to the initiation of the treatment.

10. The method of claim 1, wherein the individual does not show a symptom of hypersensitivity prior to the initiation of the treatment.

11. The method of claim 1, wherein the individual does not show a symptom resulting from the recurrent cancer upon completion of the treatment.

12. The method of claim 1, wherein the individual has a reduced CA-125 level upon completion of the treatment.

13. The method of claim 1, wherein the nanoparticles comprise the taxane coated with a coating comprising the carrier protein.

14. The method of claim 13, wherein the taxane is paclitaxel.

15. The method of claim 13, wherein the carrier protein is albumin.

16. The method of claim 1, wherein the nanoparticles composition is administered intravenously.

17. The method of claim 1, wherein the nanoparticle composition is administered intraperitoneally.

18. The method of claim 7, wherein the nanoparticles comprise the taxane coated with a coating comprising the carrier protein.

19. The method of claim 18, wherein the taxane is paclitaxel.

20. The method of claim 18, wherein the carrier protein is albumin.

21. The method of claim 19, wherein the carrier protein is albumin.

22. The method of claim 7, wherein the nanoparticles composition is administered intravenously.

23. The method of claim 7, wherein the nanoparticle composition is administered intraperitoneally.

24. The method of claim 8, wherein the nanoparticles composition is administered intravenously.

25. The method of claim 8, wherein the nanoparticle composition is administered intraperitoneally.

26. The method of claim 21, wherein the nanoparticles composition is administered intravenously.

27. The method of claim 21, wherein the nanoparticle composition is administered intraperitoneally.

28. The method of claim 1, wherein the composition comprising nanoparticles comprising a taxane and a carrier protein is administered at a single dose of about 180 mg/m$^2$ to about 300 mg/m$^2$ every three weeks.

29. The method of claim 1, wherein the composition comprising nanoparticles comprising a taxane and a carrier protein is administered at a single dose of about 260 mg/m$^2$ every three weeks.

* * * * *